(12) United States Patent
Kondoh et al.

(10) Patent No.: US 7,317,085 B2
(45) Date of Patent: Jan. 8, 2008

(54) HUMAN APOPTOSIS-ASSOCIATED GENES AND HUMAN APOPTOSIS-ASSOCIATED PROTEINS PRODUCED THEREBY

(76) Inventors: Shinae Kondoh, 18, Okazakikitagosho-cho, Sakyo-ku, Kyoto-shi, Kyoto (JP); Nobutake Akiyama, 39-8, Kamigamominamioji-cho, Kita-ku, Kyoto-shi, Kyoto (JP)

( * ) Notice: Subject to any disclaimer, the term of this patent is extended or adjusted under 35 U.S.C. 154(b) by 528 days.

(21) Appl. No.: 10/239,516

(22) PCT Filed: Jan. 22, 2002

(86) PCT No.: PCT/JP02/00413

§ 371 (c)(1),
(2), (4) Date: Oct. 29, 2002

(87) PCT Pub. No.: WO02/057444

PCT Pub. Date: Jul. 25, 2002

(65) Prior Publication Data

US 2003/0207291 A1    Nov. 6, 2003

(30) Foreign Application Priority Data

Jan. 22, 2001  (JP)  ............................. 2001-013217
May 11, 2001  (JP)  ............................. 2001-141490

(51) Int. Cl.
    *C07K 1/00*    (2006.01)

(52) U.S. Cl. ....................................................... 530/350
(58) Field of Classification Search ................. 530/350
    See application file for complete search history.

(56) References Cited

FOREIGN PATENT DOCUMENTS

| EP | 1074617 |   | 2/2001 |
|----|---------|---|--------|
| WO | WO99/40225 | * | 8/1999 |
| WO | 00/55175 |   | 9/2000 |
| WO | 01/53312 |   | 7/2001 |

OTHER PUBLICATIONS

Ishiguro et al (Oncogene, Aug. 16, 2001, 20:5062-5066).*
Tockman et al (Cancer Res., 1992, 52:2711s-2718s).*
Gura (Science, 1997, 278:1041-1042.).*
N. Akiyama et al., Identification of a Series of Transforming Growth Factor β-Responsive Genes by Retrovirus-Mediated Gene Trap Screening, Molecular and Cellular Biology, May 2000, vol. 20, No. 9, pp. 3266-3273.

* cited by examiner

*Primary Examiner*—Misook Yu
*Assistant Examiner*—Sean E Aeder
(74) *Attorney, Agent, or Firm*—Wenderoth, Lind & Ponack, L.L.P.

(57) ABSTRACT

As novel human apoptosis-related protein inducing apoptosis, a protein comprising the amino acid sequence of SEQ ID No. 2, 4 or 6 is provided. Moreover, a polynucleotide encoding the protein, an antibody against the protein, etc. are provided. These protein, polynucleotide and antibody are useful in, for example, diagnosis and treatment of cancers, autoimmune diseases, etc.

3 Claims, 10 Drawing Sheets

293/FITC-Annexin V

NTERA-2/FITC-Annexin V

293/GFP

293/GFP-TAIP-2

Full

N-half

C-half

293/GFP-TAIP-3

SEQUENCE LISTING

```
<160> NUMBER OF SEQ ID NOS: 37

<210> SEQ ID NO 1
<211> LENGTH: 2593
<212> TYPE: DNA
<213> ORGANISM: Homo sapiens
<220> FEATURE:
<221> NAME/KEY: CDS
<222> LOCATION: (107)..(1873)

<400> SEQUENCE: 1
gggcaggaga gcattccagt cgagaagacc ggctgcagta aaagcgtgag ggtggaaacg        60
ctcgaggctg tctgtcccca gacccagag cacgtccggc accacc atg act ggg         115
                                                 Met Thr Gly
                                                   1 ctg ttg aag agg aaa ttt gac cag ctg gat gag gac aac tcc tcg gtc       163
Leu Leu Lys Arg Lys Phe Asp Gln Leu Asp Glu Asp Asn Ser Ser Val
      5                  10                  15 tcc tcc tcc tcc tct tcc tct ggg tgc cag tct cgc tcc tgc tcc cca       211
Ser Ser Ser Ser Ser Ser Gly Cys Gln Ser Arg Ser Cys Ser Pro
 20                  25                  30                  35 agc tct tct gtc tcc cgt gcc tgg gac tca gag gag gaa ggc ccc tgg       259
Ser Ser Ser Val Ser Arg Ala Trp Asp Ser Glu Glu Glu Gly Pro Trp
              40                  45                  50
```

```
                                                                    -continued gat cag atg ccc ctg cct gac cgt gac ttc tgc ggc ccc aga agt ttc       307
Asp Gln Met Pro Leu Pro Asp Arg Asp Phe Cys Gly Pro Arg Ser Phe
             55                  60                  65 acc ccc ctg tct atc ctg aag cga gct cgc cgg gag cgc cca ggc cgt       355
Thr Pro Leu Ser Ile Leu Lys Arg Ala Arg Arg Glu Arg Pro Gly Arg
         70                  75                  80 gta gcc ttt gat ggg atc acc gtc ttc tac ttc ccc cgc tgc cag ggc       403
Val Ala Phe Asp Gly Ile Thr Val Phe Tyr Phe Pro Arg Cys Gln Gly
 85                  90                  95 ttc acc agt gtg ccc agc cgt ggt ggc tgt act ctg ggt atg gcc ctt       451
Phe Thr Ser Val Pro Ser Arg Gly Gly Cys Thr Leu Gly Met Ala Leu
100                 105                 110                 115 cgc cac agt gct tgc cgt cgc ttc tct ttg gct gag ttt gcg cag gag       499
Arg His Ser Ala Cys Arg Arg Phe Ser Leu Ala Glu Phe Ala Gln Glu
                120                 125                 130 caa gcc cgt gca cgg cac gag aag ctc cgc cag cgc ttg aaa gag gag       547
Gln Ala Arg Ala Arg His Glu Lys Leu Arg Gln Arg Leu Lys Glu Glu
            135                 140                 145 aag ttg gag atg ctg cag tgg aag ctt tcg gca gct ggg gta ccc cag       595
Lys Leu Glu Met Leu Gln Trp Lys Leu Ser Ala Ala Gly Val Pro Gln
        150                 155                 160 gca gag gca ggg ctg cca cct gtg gtg gat gcc att gat gac gcc tct       643
Ala Glu Ala Gly Leu Pro Pro Val Val Asp Ala Ile Asp Asp Ala Ser
    165                 170                 175 gtg gag gag gac ttg gca gtc gct gtg gca ggt ggc cgg ttg gaa gaa       691
Val Glu Glu Asp Leu Ala Val Ala Val Ala Gly Gly Arg Leu Glu Glu
180                 185                 190                 195 gtg agc ttc cta cag ccc tac cca gcc cgg cga cgt cga gct ctg ctg       739
Val Ser Phe Leu Gln Pro Tyr Pro Ala Arg Arg Arg Arg Ala Leu Leu
                200                 205                 210 agg gct tca ggt gtg cga agg atc gat cgg gag gag aag cgg gag ctg       787
Arg Ala Ser Gly Val Arg Arg Ile Asp Arg Glu Glu Lys Arg Glu Leu
            215                 220                 225 cag gca ctg cgc caa tcc cgg gag gat tgt ggc tgt cac tgc gat agg       835
Gln Ala Leu Arg Gln Ser Arg Glu Asp Cys Gly Cys His Cys Asp Arg
        230                 235                 240 atc tgc gac cct gag acc tgc agc tgc agc ctg gca ggc atc aag tgc       883
Ile Cys Asp Pro Glu Thr Cys Ser Cys Ser Leu Ala Gly Ile Lys Cys
    245                 250                 255 cag atg gac cac aca gca ttc ccc tgt ggc tgc tgc agg gag ggc tgt       931
Gln Met Asp His Thr Ala Phe Pro Cys Gly Cys Cys Arg Glu Gly Cys
260                 265                 270                 275 gag aac ccc atg ggc cgt gtg gaa ttt aat cag gca aga gtt cag acc       979
Glu Asn Pro Met Gly Arg Val Glu Phe Asn Gln Ala Arg Val Gln Thr
                280                 285                 290 cat ttc atc cac aca ctc acc cgc ctg cag ttg gaa cag gag gct gag      1027
His Phe Ile His Thr Leu Thr Arg Leu Gln Leu Glu Gln Glu Ala Glu
            295                 300                 305 agc ttt agg gag ctg gag gcc cct gcc cag ggc agc cca ccc agc cct      1075
Ser Phe Arg Glu Leu Glu Ala Pro Ala Gln Gly Ser Pro Pro Ser Pro
        310                 315                 320 ggt gag gag gcc ctg gtc cct act ttc cca ctg gcc aag ccc ccc atg      1123
Gly Glu Glu Ala Leu Val Pro Thr Phe Pro Leu Ala Lys Pro Pro Met
    325                 330                 335 aac aat gag ctg gga gac aac agc tgc agc agc gac atg act gat tct      1171
Asn Asn Glu Leu Gly Asp Asn Ser Cys Ser Ser Asp Met Thr Asp Ser
340                 345                 350                 355 tcc aca gca tct tca tca gca tcg ggc act agt gag gct cct gac tgc      1219
Ser Thr Ala Ser Ser Ser Ala Ser Gly Thr Ser Glu Ala Pro Asp Cys
```

```
                360              365              370
ccc acc cac cca ggc ctg cct ggc cct ggc ttc cag cct ggc gtt gat     1267
Pro Thr His Pro Gly Leu Pro Gly Pro Gly Phe Gln Pro Gly Val Asp
            375              380              385 gat gac agc ctg gca cgc atc ttg agt ttc agt gac tct gac ttc ggt     1315
Asp Asp Ser Leu Ala Arg Ile Leu Ser Phe Ser Asp Ser Asp Phe Gly
        390              395              400 ggg gag gag gag gaa gag gag gaa ggg agt gtg ggg aac ctg gac aac     1363
Gly Glu Glu Glu Glu Glu Glu Glu Gly Ser Val Gly Asn Leu Asp Asn
    405              410              415 ctc agc tgc ttc cat cca gct gac atc ttt ggt act agt gac cct ggt     1411
Leu Ser Cys Phe His Pro Ala Asp Ile Phe Gly Thr Ser Asp Pro Gly
420              425              430              435 ggc ctg gcc agc tgg acc cac agc tat tct ggc tgt agc ttc aca tca     1459
Gly Leu Ala Ser Trp Thr His Ser Tyr Ser Gly Cys Ser Phe Thr Ser
                440              445              450 ggc atc ctg gat gag aat gcc aac ctg gat gcc agc tgc ttc cta aat     1507
Gly Ile Leu Asp Glu Asn Ala Asn Leu Asp Ala Ser Cys Phe Leu Asn
            455              460              465 ggt ggc ctt gaa ggg tca agg gaa ggc agc ctt cct ggc acc tca gtg     1555
Gly Gly Leu Glu Gly Ser Arg Glu Gly Ser Leu Pro Gly Thr Ser Val
        470              475              480 cca ccc agc atg gac gct ggc cgg agt agc tca gtg gat ctc agc ttg     1603
Pro Pro Ser Met Asp Ala Gly Arg Ser Ser Ser Val Asp Leu Ser Leu
    485              490              495 tct tct tgt gac tcc ttt gag tta ctc cag gct ctg cca gat tat agt     1651
Ser Ser Cys Asp Ser Phe Glu Leu Leu Gln Ala Leu Pro Asp Tyr Ser
500              505              510              515 ctg ggg cct cac tac aca tca cag aag gtg tct gac agc ctg gac aac     1699
Leu Gly Pro His Tyr Thr Ser Gln Lys Val Ser Asp Ser Leu Asp Asn
                520              525              530 atc gag gca cct cac ttc ccc ctg cct ggc ctg tct cca cct ggg gat     1747
Ile Glu Ala Pro His Phe Pro Leu Pro Gly Leu Ser Pro Pro Gly Asp
            535              540              545 gcc agc agt tgc ttc ctg gag tcc ctc atg ggc ttc tcc gag cca gcc     1795
Ala Ser Ser Cys Phe Leu Glu Ser Leu Met Gly Phe Ser Glu Pro Ala
        550              555              560 gcc gaa gcc cta gat ccc ttt att gac agc cag ttt gag gac act gtc     1843
Ala Glu Ala Leu Asp Pro Phe Ile Asp Ser Gln Phe Glu Asp Thr Val
    565              570              575 cca gca tct cta atg gag cct gtg ccg gtg tgaggaccag gatgtctttt       1893
Pro Ala Ser Leu Met Glu Pro Val Pro Val
580              585 cccagcccca agagacctgt tgctgctttc ttgtaattat ggggctcccc agagtctgcg   1953
taacagtctc ccactggctg gctcacccac aggtgccatg tgcacactcc tggttttcaa   2013
acaattctct ggatttattt atttgtttta acttttctgt gctgaagaga ggactagggg   2073
gagggggctt ccccttttcag ctgcccggcc ccccacaccc acagcttgct cttctatctc   2133
cacaacgtga gcctggaaga ggagaaaatg tggctcctct ggagcttggc agaccacttt   2193
tcggtctttg cgtgatgttc cttagcccaa agacggtgag acagggctga aatcaggtgg   2253
cttctgccac cctgagccct agacccatgg gtggctaaat ccactggact gtgaagacta   2313
taatttattt ccataattta tttgagatt gaggaggctt tggttgcact tctttggctg    2373
gtgggtaatg ccaggggtgg ggtgggcaca ggccctcaag agccccttt gccttgtagt    2433 cctacacctt gccctgcctg ggctttggtg cagactaggt gtggatttga gctctgtgat   2493
ctatgtctgc tgcctggctc ctagatggct ctgcgggcag gtgctggcca aggacatcat   2553
```
ctaggcaggg ggagagcctg ggctgaacag ctgtgaccaa    2593

<210> SEQ ID NO 2
<211> LENGTH: 589
<212> TYPE: PRT
<213> ORGANISM: Homo sapiens

<400> SEQUENCE: 2

Met Thr Gly Leu Leu Lys Arg Lys Phe Asp Gln Leu Asp Glu Asp Asn
 1               5                  10                  15

Ser Ser Val Ser Ser Ser Ser Ser Ser Gly Cys Gln Ser Arg Ser
            20                  25                  30

Cys Ser Pro Ser Ser Val Ser Arg Ala Trp Asp Ser Glu Glu Glu
        35                  40                  45

Gly Pro Trp Asp Gln Met Pro Leu Pro Asp Arg Asp Phe Cys Gly Pro
 50                  55                  60

Arg Ser Phe Thr Pro Leu Ser Ile Leu Lys Arg Ala Arg Arg Glu Arg
 65                  70                  75                  80

Pro Gly Arg Val Ala Phe Asp Gly Ile Thr Val Phe Tyr Phe Pro Arg
                85                  90                  95

Cys Gln Gly Phe Thr Ser Val Pro Ser Arg Gly Gly Cys Thr Leu Gly
                100                 105                 110

Met Ala Leu Arg His Ser Ala Cys Arg Arg Phe Ser Leu Ala Glu Phe
            115                 120                 125

Ala Gln Glu Gln Ala Arg Ala Arg His Glu Lys Leu Arg Gln Arg Leu
130                 135                 140

Lys Glu Glu Lys Leu Glu Met Leu Gln Trp Lys Leu Ser Ala Ala Gly
145                 150                 155                 160

Val Pro Gln Ala Glu Ala Gly Leu Pro Pro Val Val Asp Ala Ile Asp
                165                 170                 175

Asp Ala Ser Val Glu Glu Asp Leu Ala Val Ala Val Ala Gly Gly Arg
            180                 185                 190

Leu Glu Glu Val Ser Phe Leu Gln Pro Tyr Pro Ala Arg Arg Arg Arg
        195                 200                 205

Ala Leu Leu Arg Ala Ser Gly Val Arg Arg Ile Asp Arg Glu Glu Lys
    210                 215                 220

Arg Glu Leu Gln Ala Leu Arg Gln Ser Arg Glu Asp Cys Gly Cys His
225                 230                 235                 240

Cys Asp Arg Ile Cys Asp Pro Glu Thr Cys Ser Cys Ser Leu Ala Gly
                245                 250                 255

Ile Lys Cys Gln Met Asp His Thr Ala Phe Pro Cys Gly Cys Cys Arg
            260                 265                 270

Glu Gly Cys Glu Asn Pro Met Gly Arg Val Glu Phe Asn Gln Ala Arg
        275                 280                 285

Val Gln Thr His Phe Ile His Thr Leu Thr Arg Leu Gln Leu Glu Gln
    290                 295                 300

Glu Ala Glu Ser Phe Arg Glu Leu Glu Ala Pro Ala Gln Gly Ser Pro
305                 310                 315                 320

Pro Ser Pro Gly Glu Glu Ala Leu Val Pro Thr Phe Pro Leu Ala Lys
                325                 330                 335

Pro Pro Met Asn Asn Glu Leu Gly Asp Asn Ser Cys Ser Ser Asp Met
            340                 345                 350

Thr Asp Ser Ser Thr Ala Ser Ser Ser Ala Ser Gly Thr Ser Glu Ala
        355                 360                 365

```
Pro Asp Cys Pro Thr His Pro Gly Leu Pro Gly Pro Gly Phe Gln Pro
        370                 375                 380

Gly Val Asp Asp Ser Leu Ala Arg Ile Leu Ser Phe Ser Asp Ser
385                 390                 395                 400

Asp Phe Gly Gly Glu Glu Glu Glu Glu Gly Ser Val Gly Asn
                405                 410                 415

Leu Asp Asn Leu Ser Cys Phe His Pro Ala Asp Ile Phe Gly Thr Ser
            420                 425                 430

Asp Pro Gly Gly Leu Ala Ser Trp Thr His Ser Tyr Ser Gly Cys Ser
        435                 440                 445

Phe Thr Ser Gly Ile Leu Asp Glu Asn Ala Asn Leu Asp Ala Ser Cys
        450                 455                 460

Phe Leu Asn Gly Gly Leu Glu Gly Ser Arg Glu Gly Ser Leu Pro Gly
465                 470                 475                 480

Thr Ser Val Pro Pro Ser Met Asp Ala Gly Arg Ser Ser Ser Val Asp
                485                 490                 495

Leu Ser Leu Ser Ser Cys Asp Ser Phe Glu Leu Leu Gln Ala Leu Pro
            500                 505                 510

Asp Tyr Ser Leu Gly Pro His Tyr Thr Ser Gln Lys Val Ser Asp Ser
        515                 520                 525

Leu Asp Asn Ile Glu Ala Pro His Phe Pro Leu Pro Gly Leu Ser Pro
    530                 535                 540

Pro Gly Asp Ala Ser Ser Cys Phe Leu Glu Ser Leu Met Gly Phe Ser
545                 550                 555                 560

Glu Pro Ala Ala Glu Ala Leu Asp Pro Phe Ile Asp Ser Gln Phe Glu
                565                 570                 575

Asp Thr Val Pro Ala Ser Leu Met Glu Pro Val Pro Val
            580                 585

<210> SEQ ID NO 3
<211> LENGTH: 2975
<212> TYPE: DNA
<213> ORGANISM: Homo sapiens
<220> FEATURE:
<221> NAME/KEY: CDS
<222> LOCATION: (264)..(2018)

<400> SEQUENCE: 3
aaaaaaagag ggtgggtcga cccacgcgtc cggtctttgt gcagagtgaa gctcttgttg      60
ctgaacaata aagcatatgg tacaagcaat aaaacacagg gctgggaaat ttaagaagat     120
tcctctgaac caggaagaac tgtgtcttcg gtgatgctga cacatatgat aaaatgatca     180
tttattttgg atcctaatga ataaagagtg caaggactaa gactacagtt atttgaacag     240
gtacatgtga cagcactgca gcg atg agt gga att tta aag agg aag ttt gaa     293
                        Met Ser Gly Ile Leu Lys Arg Lys Phe Glu
                          1               5                  10 gaa gtt gac ggc tcc tca ccc tgc tcc tct gtg agg gaa tca gat gat     341
Glu Val Asp Gly Ser Ser Pro Cys Ser Ser Val Arg Glu Ser Asp Asp
             15                  20                  25 gaa gtt tcc agc agt gaa agt gct gac agt ggg gac agt gtc aat cca     389
Glu Val Ser Ser Ser Glu Ser Ala Asp Ser Gly Asp Ser Val Asn Pro
         30                  35                  40 tcc act tct agt cat ttt acc cct tcc tcc att ctc aaa agg gag aaa     437
Ser Thr Ser Ser His Phe Thr Pro Ser Ser Ile Leu Lys Arg Glu Lys
     45                  50                  55 cga ctg agg aca aag aat gta cat ttt agt tgt gtc acc gtg tac tac     485
```

```
              Arg Leu Arg Thr Lys Asn Val His Phe Ser Cys Val Thr Tyr Tyr
                      60                  65                  70 ttc acc agg agg caa ggc ttc aca agt gtg ccc agt caa ggg gga agc        533
Phe Thr Arg Arg Gln Gly Phe Thr Ser Val Pro Ser Gln Gly Gly Ser
 75                  80                  85                  90 acc ctg ggg atg tcc agc cgc cat aac agc gtg cgc cag tac act ctt        581
Thr Leu Gly Met Ser Ser Arg His Asn Ser Val Arg Gln Tyr Thr Leu
                     95                 100                 105 ggc gag ttt gca agg gag cag gag agg ctc cac cgg gag atg ttg aga        629
Gly Glu Phe Ala Arg Glu Gln Glu Arg Leu His Arg Glu Met Leu Arg
                    110                 115                 120 gaa cac ctt agg gag gaa aag ctg aac tcc tta aaa cta aag atg act        677
Glu His Leu Arg Glu Glu Lys Leu Asn Ser Leu Lys Leu Lys Met Thr
            125                 130                 135 aag aat ggc aca gta gaa tca gaa gaa gcc agc act ctt aca ctg gat        725
Lys Asn Gly Thr Val Glu Ser Glu Glu Ala Ser Thr Leu Thr Leu Asp
        140                 145                 150 gac att tct gat gat gac att gac ctg gac aac aca gag gta gat gag        773
Asp Ile Ser Asp Asp Asp Ile Asp Leu Asp Asn Thr Glu Val Asp Glu
155                 160                 165                 170 tac ttc ttc cta caa cct ttg cca aca aaa aaa cga aga gct ctg ctg        821
Tyr Phe Phe Leu Gln Pro Leu Pro Thr Lys Lys Arg Arg Ala Leu Leu
                175                 180                 185 cgt gcc tct gga gtg aaa aag att gac gtg gaa gaa aag cac gaa ctc        869
Arg Ala Ser Gly Val Lys Lys Ile Asp Val Glu Glu Lys His Glu Leu
                190                 195                 200 cga gcc atc cgc ctc tca cga gag gac tgt ggc tgt gac tgc cga gtg        917
Arg Ala Ile Arg Leu Ser Arg Glu Asp Cys Gly Cys Asp Cys Arg Val
            205                 210                 215 ttc tgt gat cca gac acg tgc acc tgc agc ctg gct ggc att aag tgc        965
Phe Cys Asp Pro Asp Thr Cys Thr Cys Ser Leu Ala Gly Ile Lys Cys
        220                 225                 230 cag gtg gat cgt atg tct ttc cca tgc ggc tgc act aaa gaa gga tgt       1013
Gln Val Asp Arg Met Ser Phe Pro Cys Gly Cys Thr Lys Glu Gly Cys
235                 240                 245                 250 agt aac aca gca ggt aga att gaa ttt aat cct atc cgt gtt cgg act       1061
Ser Asn Thr Ala Gly Arg Ile Glu Phe Asn Pro Ile Arg Val Arg Thr
                255                 260                 265 cac ttt ttg cac aca ata atg aaa ctt gaa ctg gag aaa aac cga gag       1109
His Phe Leu His Thr Ile Met Lys Leu Glu Leu Glu Lys Asn Arg Glu
                270                 275                 280 cag caa atc ccc acg ctg aat ggc tgc cac agt gag ata agt gct cac       1157
Gln Gln Ile Pro Thr Leu Asn Gly Cys His Ser Glu Ile Ser Ala His
            285                 290                 295 agt agt tct atg ggc cct gtc gct cac tcc gta gaa tat tca atc gca       1205
Ser Ser Ser Met Gly Pro Val Ala His Ser Val Glu Tyr Ser Ile Ala
        300                 305                 310 gac agt ttt gag att gaa act gag ccc cag gct gca gtg ctg cac ctg       1253
Asp Ser Phe Glu Ile Glu Thr Glu Pro Gln Ala Ala Val Leu His Leu
315                 320                 325                 330 cag tcg gct gaa gaa tta gat tgc caa gga gag gag gag gaa gaa gag       1301
Gln Ser Ala Glu Glu Leu Asp Cys Gln Gly Glu Glu Glu Glu Glu Glu
                335                 340                 345 gag gat ggg agc agc ttt tgc agc gga gtc aca gat tct agc acg caa       1349
Glu Asp Gly Ser Ser Phe Cys Ser Gly Val Thr Asp Ser Ser Thr Gln
                350                 355                 360 agc ttg gca cct agt gag tca gac gag gag gag gag gaa gaa gaa gag       1397
Ser Leu Ala Pro Ser Glu Ser Asp Glu Glu Glu Glu Glu Glu Glu Glu
            365                 370                 375
```

-continued

| | | |
|---|---|---|
| gaa gag gag gag gag gat gac gat gat gac aaa gga gat ggc ttc gtg<br>Glu Glu Glu Glu Glu Asp Asp Asp Asp Asp Lys Gly Asp Gly Phe Val<br>380                         385                       390 | | 1445 |
| gaa ggt ttg ggc acc cat gcc gaa gtt gtc cct ctt cct tca gtt ctt<br>Glu Gly Leu Gly Thr His Ala Glu Val Val Pro Leu Pro Ser Val Leu<br>395                       400                    405                410 | | 1493 |
| tgt tat tct gat ggc acc gcc gtt cac gaa agc cat gca aag aat gct<br>Cys Tyr Ser Asp Gly Thr Ala Val His Glu Ser His Ala Lys Asn Ala<br>                   415                    420                    425 | | 1541 |
| tct ttt tat gcc aac tct tca act ctg tat tac caa ata gat agc cac<br>Ser Phe Tyr Ala Asn Ser Ser Thr Leu Tyr Tyr Gln Ile Asp Ser His<br>              430                       435                   440 | | 1589 |
| att cca gga act cca aat cag atc tct gag aac tat tct gaa aga gac<br>Ile Pro Gly Thr Pro Asn Gln Ile Ser Glu Asn Tyr Ser Glu Arg Asp<br>445                       450                    455 | | 1637 |
| act gtc aaa aat ggt acc ctt tcg ctg gtg cct tac acc atg acc ccg<br>Thr Val Lys Asn Gly Thr Leu Ser Leu Val Pro Tyr Thr Met Thr Pro<br>460                       465                   470 | | 1685 |
| gag caa ttc gtt gac tat gcc cga caa gca gaa gag gcc tat ggt gcc<br>Glu Gln Phe Val Asp Tyr Ala Arg Gln Ala Glu Glu Ala Tyr Gly Ala<br>475                       480                    485                490 | | 1733 |
| tcc cac tac cca gct gcc aac ccc tct gta atc gtt tgc tgc tcc tct<br>Ser His Tyr Pro Ala Ala Asn Pro Ser Val Ile Val Cys Cys Ser Ser<br>                   495                    500                   505 | | 1781 |
| tcc gaa aat gat agc ggt gtg ccc tgc aat agt tta tat cct gaa cac<br>Ser Glu Asn Asp Ser Gly Val Pro Cys Asn Ser Leu Tyr Pro Glu His<br>              510                    515                 520 | | 1829 |
| agg tcc aat cac cct caa gtg gaa ttt cac tca tac ttg aaa ggc ccc<br>Arg Ser Asn His Pro Gln Val Glu Phe His Ser Tyr Leu Lys Gly Pro<br>525                       530                    535 | | 1877 |
| tcc caa gaa ggg ttt gtc tct gca ttg aat ggt gac agt cac att tca<br>Ser Gln Glu Gly Phe Val Ser Ala Leu Asn Gly Asp Ser His Ile Ser<br>540                       545                    550 | | 1925 |
| gag cat cct gct gaa aat tct ttg agc ctt gca gaa aag agc ata ttg<br>Glu His Pro Ala Glu Asn Ser Leu Ser Leu Ala Glu Lys Ser Ile Leu<br>555                       560                    565                570 | | 1973 |
| cat gaa gag tgc atc aaa tca ccc gtg gtt gag aca gtc cct gtt<br>His Glu Glu Cys Ile Lys Ser Pro Val Val Glu Thr Val Pro Val<br>                   575                    580                585 | | 2018 |
| tagtagctta aattattcta ggaccaactc ttctcttatt taaggcactg tatttaattg | | 2078 |
| gatttcctgg gctcatcatt ggttaaactg aagaccaaga aaacttggac ggtggttaat | | 2138 |
| cttccagact gtattttgtt ttttcctttc tagccacatg actgtggcat tgcacaaata | | 2198 |
| cagtctctgt agggatttta aaagatttca gactgttttg atagaaaaag ctaaatttta | | 2258 |
| aaatgcatat ctcacagttg cctacctgtc aaactgtgtg aaacctgcca atctgtgtag | | 2318 |
| atcagagctc caaattttgg attatcgggc ctgtgcaaga ttgttaacta aggctgggaa | | 2378 |
| ataataagat ttagagtcct aattttcaat atatctgaag ataatgatga cttttttaatg | | 2438 |
| taaaagtaat tattgtaaga aaaagattta attgttccat gtgtatttta tttatggtag | | 2498 |
| tttagaagac atgttttgat gaaaatgaac agccgcatgt tcattcaagc tgaagatgca | | 2558 |
| tagctagttc cacagagcat gcccacatgg attgcatctg aatccattc acatttttat | | 2618 |
| gatcatgact gatcagattt gcaaattctt aagggtgaaa taggcctatt tttgctattt | | 2678 |
| tggacaaata aatgattcta tatgtgcagg tccttacaca cttttctcta aagttaagag | | 2738 |
| ttaggacaat cctctgggga gagtctagtt cactgccctc cctcagctga ctccagagat | | 2798 |
| ggaggtagaa ggaattgcct ttctttttta aacagcatca tcttgattct tagcttggac | | 2858 |

```
agcaccttta agctctaccc cctacatcaa aatgcacttt agtgcccctt cacggtacct    2918
cgtgtggggt ggggactgag aactctttga gatgaaaaaa tttaaaaaaa aaaaaaa      2975
```

<210> SEQ ID NO 4
<211> LENGTH: 585
<212> TYPE: PRT
<213> ORGANISM: Homo sapiens

<400> SEQUENCE: 4

```
Met Ser Gly Ile Leu Lys Arg Lys Phe Glu Glu Val Asp Gly Ser Ser
 1               5                  10                  15

Pro Cys Ser Ser Val Arg Glu Ser Asp Asp Glu Val Ser Ser Ser Glu
            20                  25                  30

Ser Ala Asp Ser Gly Asp Ser Val Asn Pro Ser Thr Ser Ser His Phe
        35                  40                  45

Thr Pro Ser Ser Ile Leu Lys Arg Glu Lys Arg Leu Arg Thr Lys Asn
    50                  55                  60

Val His Phe Ser Cys Val Thr Val Tyr Tyr Phe Thr Arg Arg Gln Gly
65                  70                  75                  80

Phe Thr Ser Val Pro Ser Gln Gly Gly Ser Thr Leu Gly Met Ser Ser
                85                  90                  95

Arg His Asn Ser Val Arg Gln Tyr Thr Leu Gly Glu Phe Ala Arg Glu
            100                 105                 110

Gln Glu Arg Leu His Arg Glu Met Leu Arg Glu His Leu Arg Glu Glu
        115                 120                 125

Lys Leu Asn Ser Leu Lys Leu Lys Met Thr Lys Asn Gly Thr Val Glu
    130                 135                 140

Ser Glu Glu Ala Ser Thr Leu Thr Leu Asp Asp Ile Ser Asp Asp Asp
145                 150                 155                 160

Ile Asp Leu Asp Asn Thr Glu Val Asp Glu Tyr Phe Phe Leu Gln Pro
                165                 170                 175

Leu Pro Thr Lys Lys Arg Arg Ala Leu Leu Arg Ala Ser Gly Val Lys
            180                 185                 190

Lys Ile Asp Val Glu Glu Lys His Glu Leu Arg Ala Ile Arg Leu Ser
        195                 200                 205

Arg Glu Asp Cys Gly Cys Asp Cys Arg Val Phe Cys Asp Pro Asp Thr
    210                 215                 220

Cys Thr Cys Ser Leu Ala Gly Ile Lys Cys Gln Val Asp Arg Met Ser
225                 230                 235                 240

Phe Pro Cys Gly Cys Thr Lys Glu Gly Cys Ser Asn Thr Ala Gly Arg
                245                 250                 255

Ile Glu Phe Asn Pro Ile Arg Val Arg Thr His Phe Leu His Thr Ile
            260                 265                 270

Met Lys Leu Glu Leu Glu Lys Asn Arg Glu Gln Ile Pro Thr Leu
        275                 280                 285

Asn Gly Cys His Ser Glu Ile Ser Ala His Ser Ser Met Gly Pro
    290                 295                 300

Val Ala His Ser Val Glu Tyr Ser Ile Ala Asp Ser Phe Glu Ile Glu
305                 310                 315                 320

Thr Glu Pro Gln Ala Ala Val Leu His Leu Ser Ala Glu Glu Leu
                325                 330                 335

Asp Cys Gln Gly Glu Glu Glu Glu Glu Glu Asp Gly Ser Ser Phe
            340                 345                 350
```

-continued

```
Cys Ser Gly Val Thr Asp Ser Ser Thr Gln Ser Leu Ala Pro Ser Glu
            355                 360                 365

Ser Asp Glu Glu Glu Glu Glu Glu Glu Glu Glu Glu Glu Glu Glu Asp
    370                 375                 380

Asp Asp Asp Lys Gly Asp Gly Phe Val Glu Gly Leu Gly Thr His
385                 390                 395                 400

Ala Glu Val Val Pro Leu Pro Ser Val Leu Cys Tyr Ser Asp Gly Thr
                405                 410                 415

Ala Val His Glu Ser His Ala Lys Asn Ala Ser Phe Tyr Ala Asn Ser
            420                 425                 430

Ser Thr Leu Tyr Tyr Gln Ile Asp Ser His Ile Pro Gly Thr Pro Asn
        435                 440                 445

Gln Ile Ser Glu Asn Tyr Ser Glu Arg Asp Thr Val Lys Asn Gly Thr
    450                 455                 460

Leu Ser Leu Val Pro Tyr Thr Met Thr Pro Glu Gln Phe Val Asp Tyr
465                 470                 475                 480

Ala Arg Gln Ala Glu Glu Ala Tyr Gly Ala Ser His Tyr Pro Ala Ala
                485                 490                 495

Asn Pro Ser Val Ile Val Cys Cys Ser Ser Glu Asn Asp Ser Gly
            500                 505                 510

Val Pro Cys Asn Ser Leu Tyr Pro Glu His Arg Ser Asn His Pro Gln
        515                 520                 525

Val Glu Phe His Ser Tyr Leu Lys Gly Pro Ser Gln Glu Gly Phe Val
    530                 535                 540

Ser Ala Leu Asn Gly Asp Ser His Ile Ser Glu His Pro Ala Glu Asn
545                 550                 555                 560

Ser Leu Ser Leu Ala Glu Lys Ser Ile Leu His Glu Glu Cys Ile Lys
                565                 570                 575

Ser Pro Val Val Glu Thr Val Pro Val
            580                 585

<210> SEQ ID NO 5
<211> LENGTH: 1682
<212> TYPE: DNA
<213> ORGANISM: Homo sapiens
<220> FEATURE:
<221> NAME/KEY: CDS
<222> LOCATION: (28)..(1656)

<400> SEQUENCE: 5
ctccccaagg aaacccctt gaaacca atg gat gca ttc acg ggc tcg ggt ctc         54
                                Met Asp Ala Phe Thr Gly Ser Gly Leu
                                  1               5 aag agg aag ttt gat gat gtg gat gtg ggc tca tca gtt tcc aac tca        102
Lys Arg Lys Phe Asp Asp Val Asp Val Gly Ser Ser Val Ser Asn Ser
 10                  15                  20                  25 gat gat gag atc tcc agc agt gat agt gct gac agc tgc gac agc ctc        150
Asp Asp Glu Ile Ser Ser Ser Asp Ser Ala Asp Ser Cys Asp Ser Leu
                 30                  35                  40 aat cct cct acc act gcc agc ttc aca ccc aca tcc atc ctg aag cgg        198
Asn Pro Pro Thr Thr Ala Ser Phe Thr Pro Thr Ser Ile Leu Lys Arg
             45                  50                  55 cag aag cag ctg cgg agg aag aat gta cgc ttt gac cag gtg act gta        246
Gln Lys Gln Leu Arg Arg Lys Asn Val Arg Phe Asp Gln Val Thr Val
         60                  65                  70 tac tac ttt gcc cgg cgc caa ggt ttt acc agt gtg ccc agc cag ggt        294
Tyr Tyr Phe Ala Arg Arg Gln Gly Phe Thr Ser Val Pro Ser Gln Gly
     75                  80                  85
```

```
                                                                          -continued ggt agc tct ctg ggc atg gcc cag cgc cat aac tct gta cgg agc tat          342
Gly Ser Ser Leu Gly Met Ala Gln Arg His Asn Ser Val Arg Ser Tyr
 90              95                 100                 105 aca ctc tgt gag ttt gcc cag gaa cag gag gtg aac cat cga gag att          390
Thr Leu Cys Glu Phe Ala Gln Glu Gln Glu Val Asn His Arg Glu Ile
                110                 115                 120 ctg cgt gag cac ctg aag gaa gag aaa ctc cat gcc aag aaa atg aag          438
Leu Arg Glu His Leu Lys Glu Glu Lys Leu His Ala Lys Lys Met Lys
            125                 130                 135 ctg acc aag aat ggg aca gtg gag tcg gtg gag gct gat ggc ctg acg          486
Leu Thr Lys Asn Gly Thr Val Glu Ser Val Glu Ala Asp Gly Leu Thr
        140                 145                 150 ctg gat gat gtg tca gat gaa gat att gat gtg gaa aat gtg gag gtg          534
Leu Asp Asp Val Ser Asp Glu Asp Ile Asp Val Glu Asn Val Glu Val
    155                 160                 165 gat gat tac ttc ttc ctg cag cct ctg ccc acc aaa cgg cga cgg gcc          582
Asp Asp Tyr Phe Phe Leu Gln Pro Leu Pro Thr Lys Arg Arg Arg Ala
170                 175                 180                 185 ctg ctg agg gct tct ggg gtc cac cgt att gat gct gaa gag aag caa          630
Leu Leu Arg Ala Ser Gly Val His Arg Ile Asp Ala Glu Glu Lys Gln
                190                 195                 200 gaa ctt cga gcc atc cgc ctg tca cgg gaa gaa tgt ggt tgt gac tgc          678
Glu Leu Arg Ala Ile Arg Leu Ser Arg Glu Glu Cys Gly Cys Asp Cys
            205                 210                 215 cga ctg tat tgt gac cca gaa gcg tgt gcc tgc agc cag gct ggg att          726
Arg Leu Tyr Cys Asp Pro Glu Ala Cys Ala Cys Ser Gln Ala Gly Ile
        220                 225                 230 aaa tgc cag gtg gat cgc atg tcc ttt cca tgt ggc tgc tcc cgg gat          774
Lys Cys Gln Val Asp Arg Met Ser Phe Pro Cys Gly Cys Ser Arg Asp
    235                 240                 245 ggc tgt ggg aac atg gca gga cgc att gaa ttt aat cca atc cgg gtc          822
Gly Cys Gly Asn Met Ala Gly Arg Ile Glu Phe Asn Pro Ile Arg Val
250                 255                 260                 265 cgg act cat tac ctc cac acc att atg aag ctg gag ctg gag agc aag          870
Arg Thr His Tyr Leu His Thr Ile Met Lys Leu Glu Leu Glu Ser Lys
                270                 275                 280 cgg cag gtg agc cgc cca gca gcc cca gat gag gag ccc tcc ccg act          918
Arg Gln Val Ser Arg Pro Ala Ala Pro Asp Glu Glu Pro Ser Pro Thr
            285                 290                 295 gcc agt tgc agc ctg aca gga gca cag ggc tct gag acc cag gac ttc          966
Ala Ser Cys Ser Leu Thr Gly Ala Gln Gly Ser Glu Thr Gln Asp Phe
        300                 305                 310 cag gag ttc att gct gag aat gag aca gca gtg atg cac ctg cag agt         1014
Gln Glu Phe Ile Ala Glu Asn Glu Thr Ala Val Met His Leu Gln Ser
    315                 320                 325 gca gag gaa ctg gag cgg ctc aag gca gaa gaa gat tcc agc ggc tct         1062
Ala Glu Glu Leu Glu Arg Leu Lys Ala Glu Glu Asp Ser Ser Gly Ser
330                 335                 340                 345 agt gcc agc ctg gac tcg agc atc gag agc ctg ggt gtg tgc atc cta         1110
Ser Ala Ser Leu Asp Ser Ser Ile Glu Ser Leu Gly Val Cys Ile Leu
                350                 355                 360 gag gag cct ctg gct gtc ccc gaa gag ctg tgc cca ggc ctt aca gcc         1158
Glu Glu Pro Leu Ala Val Pro Glu Glu Leu Cys Pro Gly Leu Thr Ala
            365                 370                 375 ccc att ctc atc cag gct cag ctg ccc cca ggc tcc tct gtc ctg tgt         1206
Pro Ile Leu Ile Gln Ala Gln Leu Pro Pro Gly Ser Ser Val Leu Cys
        380                 385                 390 ttt acc gag aac tca gac cac cca act gcc tca acg gtg aac agc cca         1254
Phe Thr Glu Asn Ser Asp His Pro Thr Ala Ser Thr Val Asn Ser Pro
```

-continued

```
              395                 400                 405
tcc tac ttg aac agt ggg ccc ctg gtc tat tat caa gtg gag cag agg      1302
Ser Tyr Leu Asn Ser Gly Pro Leu Val Tyr Tyr Gln Val Glu Gln Arg
410                 415                 420                 425 cca gtc ttg gga gtg aaa gga gag cct ggt acg gaa gaa ggc tca gcc      1350
Pro Val Leu Gly Val Lys Gly Glu Pro Gly Thr Glu Glu Gly Ser Ala
                430                 435                 440 tct ttc cca aag gag aag gat ctg aat gtc ttc tct ctc cct gtt acc      1398
Ser Phe Pro Lys Glu Lys Asp Leu Asn Val Phe Ser Leu Pro Val Thr
            445                 450                 455 tca ctc gtg gct tgt agc tcc aca gac cca gct gcc ctc tgt aaa tca      1446
Ser Leu Val Ala Cys Ser Ser Thr Asp Pro Ala Ala Leu Cys Lys Ser
        460                 465                 470 gag gtg ggg aaa aca ccc acc cta gaa gct cta ttg ccc gaa gat tgt      1494
Glu Val Gly Lys Thr Pro Thr Leu Glu Ala Leu Leu Pro Glu Asp Cys
    475                 480                 485 aac cct gag gag cct gaa aat gaa gac ttc cac cct tcc tgg tcc ccc      1542
Asn Pro Glu Glu Pro Glu Asn Glu Asp Phe His Pro Ser Trp Ser Pro
490                 495                 500                 505 tca agc ctc ccc ttc cgc acg gac aat gaa gag ggc tgt ggg atg gtg      1590
Ser Ser Leu Pro Phe Arg Thr Asp Asn Glu Glu Gly Cys Gly Met Val
                510                 515                 520 aag acc tcc cag cag aat gag gat cgg ccc cct gaa gat tct tcc tta      1638
Lys Thr Ser Gln Gln Asn Glu Asp Arg Pro Pro Glu Asp Ser Ser Leu
            525                 530                 535 gaa ctc cct ctg gca gtg tgacagacca cgcgtgccct atagtg                 1682
Glu Leu Pro Leu Ala Val
        540

<210> SEQ ID NO 6
<211> LENGTH: 543
<212> TYPE: PRT
<213> ORGANISM: Homo sapiens

<400> SEQUENCE: 6

Met Asp Ala Phe Thr Gly Ser Gly Leu Lys Arg Lys Phe Asp Asp Val
 1               5                  10                  15

Asp Val Gly Ser Ser Val Ser Asn Ser Asp Asp Glu Ile Ser Ser Ser
                20                  25                  30

Asp Ser Ala Asp Ser Cys Asp Ser Leu Asn Pro Thr Thr Ala Ser
            35                  40                  45

Phe Thr Pro Thr Ser Ile Leu Lys Arg Gln Lys Gln Leu Arg Arg Lys
        50                  55                  60

Asn Val Arg Phe Asp Gln Val Thr Val Tyr Tyr Phe Ala Arg Arg Gln
 65                  70                  75                  80

Gly Phe Thr Ser Val Pro Ser Gln Gly Gly Ser Ser Leu Gly Met Ala
                85                  90                  95

Gln Arg His Asn Ser Val Arg Ser Tyr Thr Leu Cys Glu Phe Ala Gln
                100                 105                 110

Glu Gln Glu Val Asn His Arg Glu Ile Leu Arg Glu His Leu Lys Glu
            115                 120                 125

Glu Lys Leu His Ala Lys Lys Met Lys Leu Thr Lys Asn Gly Thr Val
        130                 135                 140

Glu Ser Val Glu Ala Asp Gly Leu Thr Leu Asp Asp Val Ser Asp Glu
145                 150                 155                 160

Asp Ile Asp Val Glu Asn Val Glu Val Asp Asp Tyr Phe Phe Leu Gln
                165                 170                 175
```

-continued

```
Pro Leu Pro Thr Lys Arg Arg Ala Leu Leu Arg Ala Ser Gly Val
            180                 185                 190

His Arg Ile Asp Ala Glu Glu Lys Gln Glu Leu Arg Ala Ile Arg Leu
        195                 200                 205

Ser Arg Glu Glu Cys Gly Cys Asp Cys Arg Leu Tyr Cys Asp Pro Glu
    210                 215                 220

Ala Cys Ala Cys Ser Gln Ala Gly Ile Lys Cys Gln Val Asp Arg Met
225                 230                 235                 240

Ser Phe Pro Cys Gly Cys Ser Arg Asp Gly Cys Gly Asn Met Ala Gly
                245                 250                 255

Arg Ile Glu Phe Asn Pro Ile Arg Val Arg Thr His Tyr Leu His Thr
                260                 265                 270

Ile Met Lys Leu Glu Leu Glu Ser Lys Arg Gln Val Ser Arg Pro Ala
            275                 280                 285

Ala Pro Asp Glu Glu Pro Ser Pro Thr Ala Ser Cys Ser Leu Thr Gly
290                 295                 300

Ala Gln Gly Ser Glu Thr Gln Asp Phe Gln Glu Phe Ile Ala Glu Asn
305                 310                 315                 320

Glu Thr Ala Val Met His Leu Gln Ser Ala Glu Leu Glu Arg Leu
                325                 330                 335

Lys Ala Glu Asp Ser Ser Gly Ser Ser Ala Ser Leu Asp Ser Ser
            340                 345                 350

Ile Glu Ser Leu Gly Val Cys Ile Leu Glu Glu Pro Leu Ala Val Pro
            355                 360                 365

Glu Glu Leu Cys Pro Gly Leu Thr Ala Pro Ile Leu Ile Gln Ala Gln
    370                 375                 380

Leu Pro Pro Gly Ser Ser Val Leu Cys Phe Thr Glu Asn Ser Asp His
385                 390                 395                 400

Pro Thr Ala Ser Thr Val Asn Ser Pro Ser Tyr Leu Asn Ser Gly Pro
                405                 410                 415

Leu Val Tyr Tyr Gln Val Glu Gln Arg Pro Val Leu Gly Val Lys Gly
                420                 425                 430

Glu Pro Gly Thr Glu Glu Gly Ser Ala Ser Phe Pro Lys Glu Lys Asp
            435                 440                 445

Leu Asn Val Phe Ser Leu Pro Val Thr Ser Leu Val Ala Cys Ser Ser
450                 455                 460

Thr Asp Pro Ala Ala Leu Cys Lys Ser Glu Val Gly Lys Thr Pro Thr
465                 470                 475                 480

Leu Glu Ala Leu Leu Pro Glu Asp Cys Asn Pro Glu Pro Glu Asn
                485                 490                 495

Glu Asp Phe His Pro Ser Trp Ser Pro Ser Ser Leu Pro Phe Arg Thr
                500                 505                 510

Asp Asn Glu Glu Gly Cys Gly Met Val Lys Thr Ser Gln Gln Asn Glu
            515                 520                 525

Asp Arg Pro Pro Glu Asp Ser Ser Leu Glu Leu Pro Leu Ala Val
530                 535                 540
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 7
ctccccaagg aaacccttt gaaacca                                    27

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 8
ttggtcacag ctgttcagcc caggctctcc                                30

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 9
agatgactaa gaatggcagt agaatcag                                  28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 10
acctggcact taatgccagc caggctgcag                                30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 11
ggacgcattg aatttaatcc aatccgggtc                                30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 12
cggactcatt acctccacac cattatgaag                                30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 13

```
ctccccaagg aaaccccttt gaaaccaatg                                    30
```

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 14

```
cactataggg cacgcgtggt ctgtcacac                                     29
```

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 15

```
taaggatcca tgactgggct gttgaagagg aaattg                             36
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 16

```
taactcgagc accggcacag gctccattag aga                                33
```

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 17

```
taaggatcca tgagtggaat tttaaagagg aagt                               34
```

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 18

```
taactcgaga acagggactg tctcaaccac gggt                               34
```

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 19

```
taaggatcca tggatgcatt cacgggctcg ggtc                               34
```

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 20
taagtcgacc actgccagag ggagttctaa ggaa                           34

<210> SEQ ID NO 21
<211> LENGTH: 215
<212> TYPE: DNA
<213> ORGANISM: Artificial Sequence
<220> FEATURE:
<223> OTHER INFORMATION: Description of Artificial Sequence:
      Synthesized polynucleotide
<220> FEATURE:
<221> NAME/KEY: CDS
<222> LOCATION: (40)..(189)

<400> SEQUENCE: 21
gctagccacc gcggtggcgg ccgctctagc ccgggcacc atg gat tac aag gat   54
                                           Met Asp Tyr Lys Asp
                                             1               5 gac gac gat aag atc gga tcc gaa ttc gat atc gtc gac ctc gag atc  102
Asp Asp Asp Lys Ile Gly Ser Glu Phe Asp Ile Val Asp Leu Glu Ile
             10                  15                  20 cga gct cgg tac caa gct tac gta gaa caa aaa ctc atc tca gaa gag  150
Arg Ala Arg Tyr Gln Ala Tyr Val Glu Gln Lys Leu Ile Ser Glu Glu
         25                  30                  35 gat ctg aat agc gcc gtc gac cat cat cat cat cat cat tgagtttaaa   199
Asp Leu Asn Ser Ala Val Asp His His His His His His
     40                  45                  50 cggtctccag cttaag                                               215

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 22
taaggatccg ccgccaccat gactgggctg ttgaagagga aatttg               46

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 23
taactcgagc accggcacag gctccattag aga                             33

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence:

Synthesized oligonucleotide

<400> SEQUENCE: 24
taaggatccg ccgccaccat gagtccaatt ttaaagagga agt         43

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:
    Synthesized oligonucleotide

<400> SEQUENCE: 25
taactcgaga acagggactg tctcaaccac gggt         34

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence:
    Synthesized oligonucleotide

<400> SEQUENCE: 26
tttggatccg ccgccaccat ggatgcaggc acgggctcgg gtc         43

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence:
    Synthesized oligonucleotide

<400> SEQUENCE: 27
taagtcgacc actgccagag ggcgttctaa ggaa         34

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:
    Synthesized oligonucleotide

<400> SEQUENCE: 28
taactcgagc agggcctcct caccagggct gggt         34

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence:
    Synthesized oligonucleotide

<400> SEQUENCE: 29
taaggatccg ccgccaccat gctggtccct actttcccac tggcca         46

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence:
    Synthesized oligonucleotide -continued

```
<400> SEQUENCE: 30
tatctcgagt gcagcctggg gctcagtttc aatc                           34

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 31
taaggatccg ccgccaccat ggtgctgcac ctgcagtcgg ctgaag              46

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 32
tatagtcgac gctgcaactg gcagtcgggg aggg                           34

<210> SEQ ID NO 33
<211> LENGTH: 46
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 33
tttggatccg ccgccaccat gctgacagga gcacagggct ctgaga             46

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 34
atgactgggc tgttgaagag gaaatttgac                                30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 35
caccggcaca ggctccatta gagatgctgg                                30

<210> SEQ ID NO 36
<211> LENGTH: 216
<212> TYPE: PRT
<213> ORGANISM: Artificial Sequence
<220> FEATURE:
<223> OTHER INFORMATION: Description of Artificial Sequence:
      Synthesized polypeptide
```

<400> SEQUENCE: 36

```
Met His His His His His Arg Arg Phe Ser Leu Ala Glu Phe Ala
  1               5                  10                  15

Gln Glu Gln Ala Arg Ala Arg His Glu Lys Leu Arg Gln Arg Leu Lys
             20                  25                  30

Glu Glu Lys Leu Glu Met Leu Gln Trp Lys Leu Ser Ala Ala Gly Val
         35                  40                  45

Pro Gln Ala Glu Ala Gly Leu Pro Pro Val Val Asp Ala Ile Asp Asp
     50                  55                  60

Ala Ser Val Glu Asp Leu Ala Val Ala Gly Gly Arg Leu
 65                  70                  75                  80

Glu Glu Val Ser Phe Leu Gln Pro Tyr Pro Ala Arg Arg Arg Ala
                 85                  90                  95

Leu Leu Arg Ala Ser Gly Val Arg Arg Ile Asp Arg Glu Glu Lys Arg
            100                 105                 110

Glu Leu Gln Ala Leu Arg Gln Ser Arg Glu Asp Cys Gly Cys His Cys
        115                 120                 125

Asp Arg Ile Cys Asp Pro Glu Thr Cys Ser Cys Ser Leu Ala Gly Ile
130                 135                 140

Lys Cys Gln Met Asp His Thr Ala Phe Pro Cys Gly Cys Cys Arg Glu
145                 150                 155                 160

Gly Cys Glu Asn Pro Met Gly Arg Val Glu Phe Asn Gln Ala Arg Val
                165                 170                 175

Gln Thr His Phe Ile His Thr Leu Thr Arg Leu Gln Leu Glu Gln Glu
            180                 185                 190

Ala Glu Ser Phe Arg Glu Leu Glu Ala Pro Ala Gln Gly Ser Pro Pro
        195                 200                 205

Ser Pro Gly Glu Glu Ala Leu Val
    210                 215
```

<210> SEQ ID NO 37
<211> LENGTH: 259
<212> TYPE: PRT
<213> ORGANISM: Artificial Sequence
<220> FEATURE:
<223> OTHER INFORMATION: Description of Artificial Sequence: Synthesized polypeptide

<400> SEQUENCE: 37

```
Val Leu His Leu Gln Ser Ala Glu Glu Leu Asp Cys Gln Gly Glu Glu
  1               5                  10                  15

Glu Glu Glu Glu Glu Asp Gly Ser Ser Phe Cys Ser Gly Val Thr Asp
             20                  25                  30

Ser Ser Thr Gln Ser Leu Ala Pro Ser Glu Ser Asp Glu Glu Glu
         35                  40                  45

Glu Glu Glu Glu Glu Glu Glu Glu Asp Asp Asp Asp Lys Gly
     50                  55                  60

Asp Gly Phe Val Glu Gly Leu Gly Thr His Ala Glu Val Val Pro Leu
 65                  70                  75                  80

Pro Ser Val Leu Cys Tyr Ser Asp Gly Thr Ala Val His Glu Ser His
                 85                  90                  95

Ala Lys Asn Ala Ser Phe Tyr Ala Asn Ser Ser Thr Leu Tyr Tyr Gln
            100                 105                 110

Ile Asp Ser His Ile Pro Gly Thr Pro Asn Gln Ile Ser Glu Asn Tyr
        115                 120                 125
```

-continued

```
Ser Glu Arg Asp Thr Val Lys Asn Gly Thr Leu Ser Leu Val Pro Tyr
    130                 135                 140

Thr Met Thr Pro Glu Gln Phe Val Asp Tyr Ala Arg Gln Ala Glu Glu
145                 150                 155                 160

Ala Tyr Gly Ala Ser His Tyr Pro Ala Ala Asn Pro Ser Val Ile Val
                165                 170                 175

Cys Cys Ser Ser Ser Glu Asn Asp Ser Gly Val Pro Cys Asn Ser Leu
            180                 185                 190

Tyr Pro Glu His Arg Ser Asn His Pro Gln Val Glu Phe His Ser Tyr
        195                 200                 205

Leu Lys Gly Pro Ser Gln Glu Gly Phe Val Ser Ala Leu Asn Gly Asp
    210                 215                 220

Ser His Ile Ser Glu His Pro Ala Glu Asn Ser Leu Ser Leu Ala Glu
225                 230                 235                 240

Lys Ser Ile Leu His Glu Glu Cys Ile Lys Ser Pro Val Val Glu Thr
                245                 250                 255

Val Pro Val
```

HUMAN APOPTOSIS-ASSOCIATED GENES AND HUMAN APOPTOSIS-ASSOCIATED PROTEINS PRODUCED THEREBY

This application is a U.S. national stage of PCT/JP02/00413 filed Jan. 22, 2002.

TECHNICAL FIELD

The inventions of the present application relate to novel human apoptosis-related proteins that induce apoptosis, polynucleotides encoding the proteins, and antibodies against the proteins. The proteins and the antibodies of the inventions are useful in diagnosis and treatment of various diseases, and the polynucleotides are useful as probes for gene diagnosis and gene sources for gene therapy. Further, the polynucleotides can be used as gene sources for mass production of the proteins of the invention.

BACKGROUND ART

Apoptosis is known to have an important role in morphogenesis, homeostasis, immune protection, etc. of individuals [Bosman F T, Visser B C, van Oeveren J. (1996) Pathol. Res. Pract. 192(7): 676-83]. Further, human TGF-β is known to have various functions related with regulation of development, differentiation, growth and oncogenic transformation of cells [Massague, J. (1990). Annu. Rev. Cell Biol. 6:597-641] and to show a useful role in morphogenesis [Akhurst R J, FitzPatrick D R, Gatherer D. Lehnert S A, Millan S A, Millan F A. Prog. Growth Factor Res. (1990) 2(3):153-68]. Accordingly, proteins induced by human TGF-β and having apoptotic activity are considered to participate in morphogenesis, as well as onset and progression of cancers, immunological diseases, etc.

Proteins inducing apoptosis have a potential as target proteins for developing low-molecular pharmaceuticals intended for apoptosis, and it is required to obtain as many apoptosis-related proteins as possible.

The object of the invention is to provide novel apoptosis-related proteins inducing apoptosis of cells and genes encoding the apoptosis-related proteins, which genes are useful for development of pharmaceuticals, etc. Other object of the invention is to provide genetic manipulation materials such as polynucleotides encoding the proteins, antibodies against the proteins, etc.

DISCLOSURE OF INVENTION

The invention of the application provides a human apoptosis-related gene that encodes a human apoptosis-related protein having the amino acid sequence of SEQ ID No. 2, 4 or 6. From mRNA transcribed from this gene, cDNA having the base sequence of SEQ ID No. 1, 3 or 5 is synthesized.

The invention provides a polynucleotide purified from genomic DNA, mRNA or cDNA of the human apoptosis-related gene or a complementary sequence thereof.

The invention provides a probe hybridizing with the human apoptosis-related gene or the purified polynucleotide under stringent conditions, and a primer set for PCR amplification of the human apoptosis-related gene of claim 1 or the purified polynucleotide.

The invention provides a recombinant vector having the polynucleotide, and a transformant with the recombinant vector.

The invention provides a purified human apoptosis-related protein, which is an expression product of the human apoptosis-related gene, and has the amino acid sequence of SEQ ID No. 2, 4 or 6. As one embodiment, the protein is produced from the transformant of claim 7.

The invention provides a purified or synthesized peptide, which is a part of the human apoptosis-related protein. A preferred embodiment is a peptide consisting of at least five continuous amino acid residues of the 1st-328th amino acid sequence in SEQ ID No. 2, a peptide consisting of at least five continuous amino acid residues of the 1st-326th amino acid sequence in SEQ ID No. 4, a peptide comprising at least the 385th-389th amino acid sequence in SEQ ID No. 4, and a peptide consisting of at least five continuous amino acid residues of the 1st-301st amino acid sequence in SEQ ID No. 6.

The invention provides an antibody against the purified human apoptosis-related protein.

The invention provides a method for screening a molecule that controls an apoptotic activity of the purified human apoptosis-related protein, which comprises identifying the target molecule by using, as an index, a cleavage activity to the peptide comprising at least the 385th-389th amino acid sequence in SEQ ID No. 4.

BEST MODE FOR CARRYING OUT THE INVENTION

Figure 1:
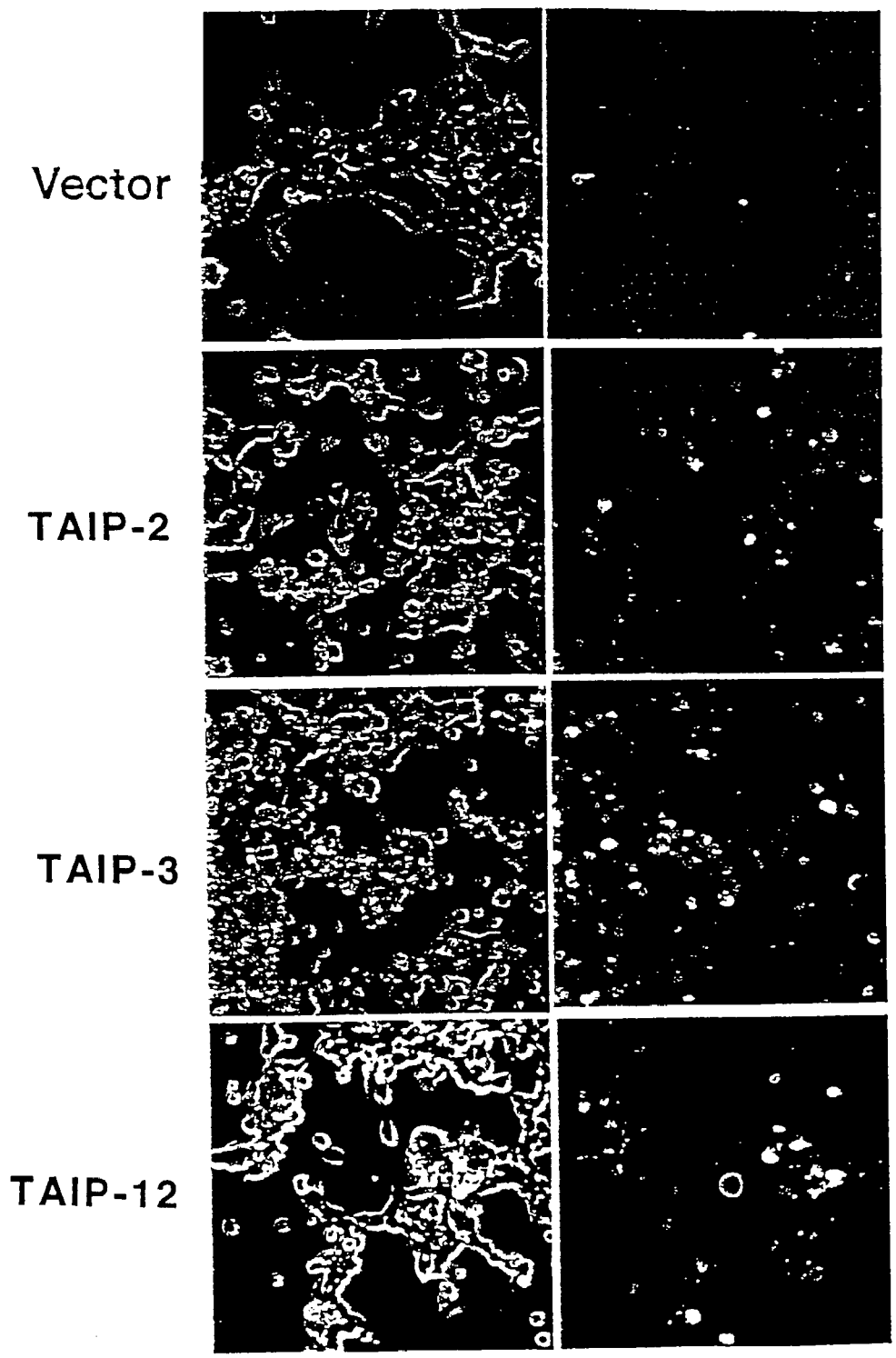
FIG. 1 is phase-contrast and fluorescent micrographs of HEK293, a human embryo kidney cell line, to which the polynucleotides encoding SEQ ID No. 2, 4 and 6 in vector (TAIP-3, TAIP-2, TAIP-12 respectively) or empty vector (vector) were transfected, and Annexin V-FITC was treated. The left panels are the phase-contrast and the right panels are fluorescent micrograph.

The human apoptosis-related genes (hereinafter sometimes referred to as TAIP genes) of the invention are genomic genes identified from human Chromosome 3, Chromosome 2 and Chromosome 12, and encoding three types of proteins having amino acid sequences of SEQ ID Nos. 2, 4 and 6 (hereinafter sometimes referred to as TAIP proteins or TAIP-3, TAIP-2 and TAIP-12 respectively). And cDNA of TAIP-3 gene has a base sequence of SEQ ID No. 1, cDNA of TAIP-2 gene has a base sequence of SEQ ID No. 3, and cDNA of TAIP-12 has a base sequence of SEQ ID No. 5.

The TAIP genes contain expression-regulating regions (promoter/enhancer and suppressor sequences, etc.) to protein encoding regions. These expression-regulating sequences are useful as, for example, materials for screening substances that regulate the in vivo expression of TAIP proteins.

The TAIP genes may be isolated by screening a human genomic DNA library using probes provided respectively by the invention. As the probes, for example, partial sequences (15 bp or more) or their complementary sequences of the purified polynucleotides (for example, cDNAs) provided by the invention can be used. The screening with the probes can be conducted under "stringent conditions" enabling specific hybridization of genomic DNAs and the probes. The stringent conditions can be defined by a salt concentration, a concentration of an organic solvent (formaldehyde, etc.), temperature conditions, etc. in hybridization and washing steps. For example, the conditions disclosed in U.S. Pat. No. 6,100,037, etc. can be employed.

The TAIP genes can also be amplified by the PCR (Polymerase Chain Reaction) method using the primer set provided by the invention with genomic DNAs as templates. The primer set can be formed by a combination of at least two partial sequences (15 bp or more) selected from the purified polynucleotides (for example, cDNAs) provided by the invention. Further, the upstream of the genes can also be PCR-amplified by the 5' RACE method using 1 primer on the 5' side of cDNAs and the downstream region of the genes by the 3'RACE method using 1 primer on the 3' side of cDNAs. For example, the following can be indicated as points to be considered in primer designing. The size (number of bases) of the primer is from 15 to 40 bases, preferably from 15 to 30 bases in consideration of satisfying the specific annealing with template DNAs, provided at least 30 bases are effective in conducting LA (long accurate) PCR. A complementary sequence between both primers is avoided lest a set or a pair (two) of primers comprising a sense chain (on the 5' end) and an antisense chain (on the 3' end) are mutually annealed, and a self complementary sequence is also avoided for inhibiting formation of a hairpin structure in the primers. Further, the GC content is set at approximately 50% for securing stable binding with template DNAs lest the GC-rich or the AT-rich be present in the primers. Since the annealing temperature depends on Tm (melting temperature), primers approximate to each other with a Tm value of from 55 to 65° C. are selected to obtain PCR products having a high specificity. Moreover, it has to be considered that the final concentration in using the primers in PCR is adjusted to from approximately 0.1 to approximately 1 μm. In addition, commercial software for primer designing, for example, Oligo™ [National Bioscience Inc. (U.S.A.)] or GENETYX [Software Kaihatsu K.K. (Japan)] can also be used.

The thus-obtained full-length genomic genes can be amplified by ordinary gene amplification methods such as a PCR method, an NASBN (Nucleic acid sequence based amplification) method, a TMA (Transcription-mediated amplification) method and an SDA (Strand Displacement Amplification) method.

The purified polynucleotides (DNA fragments or RNA fragments) can be prepared from TAIP genomic genes, mRNAs transcribed from these genes and cDNAs synthesized from the mRNAs. For example, cDNAs can be synthesized using Poly(A)+RNA extracted from human cells as a template. The human cells may be cells extracted from the human body by, for example, surgical operation or culture cells. Alternatively, desired cDNAs can also be synthesized by the RT-PCR method with mRNAs isolated from human cells as templates using the primer set provided by the invention. The thus-prepared cDNAs have specifically base sequences of SEQ ID Nos. 1, 3 and 5 respectively. These polynucleotides can be used in the genetic engineering production of TAIP proteins.

Polymorphism due to individual differences is generally often observed in human genes. Accordingly, polynucleotides with addition and deletion of one or more nucleotides and/or replacement with other nucleotides in SEQ ID Nos.

1, 3 and 5 are also included in the scope of the invention. Likewise, proteins with addition and deletion of one or more amino acids and/or replacement with other amino acids, occurring according to these changes in polynucleotides, are also included in the scope of the proteins of the invention so long as they possess an activity of proteins having amino acid sequences represented by SEQ ID Nos. 2, 4 and 6.

The recombinant vector of the invention is a cloning vector or an expression vector, and appropriate vector is used according to the type of the polynucleotide as an insert, the use purpose thereof and the like. For example, when TAIP protein is produced using cDNA or ORF region thereof as an insert, an expression vector for in vitro transcription or an expression vector suited for prokaryotic cells such as *Escherichia coli* and *Bacillus subtilis* or eukaryotic cells such as yeasts, insect cells and mammal cells can be used. Further, when genomic DNA of the TAIP gene is used as an insert, BAC (Bacterial Artificial Chromosome) vectors, cosmid vectors or the like can also be used.

As the transformant of the invention, prokaryotic cells such as *Escherichia coli* and *Bacillus subtilis*, eukaryotic cells such as yeasts, insect cells, mammal cells and the like can be used. This transformant can be prepared by introducing the recombinant vector into cells by a known method such as an electroporation method, a calcium phosphate method, a ribosome method and a DEAE dextran method.

The TAIP protein of the invention can be obtained by isolating from human organs, cell lines, etc., by chemical synthesis to prepare a peptide based on the amino acid sequence of SEQ ID No. 2, 4 or 6, and by a recombinant DNA technology using the purified polynucleotides (cDNAs or translational regions thereof) provided by the invention. The recombinant DNA technology is preferably used to obtain the protein. For example, preparing RNA from the vector having the polynucleotide through in vitro transcription and conducting in vitro translation using it as a template can express the protein in vitro. Further, when the polynucleotide is recombined into an appropriate expression vector by a known method, the protein can be mass-expressed in prokaryotic cells such as *Escherichia coli* and *Bacillus subtilis* or eukaryotic cells such as yeasts, insect cells and mammal cells.

In case of producing the TAIP protein by expressing DNA through in vitro translation, the polynucleotide is inserted into a vector having a promoter for an RNA polymerase to form a recombinant vector, and this vector is added to an in vitro translation system containing the RNA polymerase corresponding to the promoter, such as rabbit reticulocyte lysate, wheat germ extract or the like to produce the TAIP protein in vitro. Examples of the RNA polymerase promoter include T7, T3 and SP6. Examples of the vectors containing these RNA polymerase promoters can include pKA1, pCDM8, pT3/T7 18, pT7/3 19 and pBluescript II.

In case of producing the TAIP protein by expressing DNA in microorganisms such as *Escherichia coli*, an expression vector having an origin replicable in the microorganism, promoter, ribosome binding site, DNA cloning sites, terminator or the like is recombined with the foregoing polynucleotide to form a recombinant expression vector. A host cell is transformed with this expression vector, and the obtained transformant is then cultured, whereby the protein can be mass-produced in microorganisms. At this time, when the expression is conducted by adding an initiation codon and a termination codon before and after an optional translational region, a protein fragment containing the optional region can be obtained. Alternatively, it can also be expressed as a fusion protein with another protein. Only the protein portion that the polynucleotide encodes can also be obtained by cleaving this fusion protein with an appropriate protease. Examples of the expression vector for *Escherichia coli* can include pUC series, pBluescript II, pET expression system and pGEX expression system.

In case of producing the TAIP protein by expressing DNA in eukaryotic cells, the polynucleotide is inserted into an expression vector for eukaryotic cells having a promoter, a splicing region, a Poly(A) addition site, etc. to form a recombinant vector, and this recombinant vector is transfected into eukaryotic cells. Then, the TAIP protein can be produced in eukaryotic cells. Examples of the expression vector can include pKA1, pCDM8, pSVK3, pMSG, pSVL, pBK-CMV, pBK-RSV, EBV vector, pRS and pYES2. Further, when pIND/V5-His, pFLAG-CMV-2, pEGFP-N1, pEGFP-C1 and the like are used as an expression vector, the TAIP protein can also be expressed as fusion proteins with various tags such as His tag, FLAG tag and GFP added. As eukaryotic cells, mammal culture cells such as monkey renal cell line COS7 and Chinese hamster ovary cell line CHO, budding yeast, fission yeast, Bombyx mori cells, Xenopus egg cells and the like are generally used. However, any eukaryotic cells are available so long as they can express the TAIP protein. For the expression vector to be transfected into eukaryotic cells, a known method such as an electroporation method, a calcium phosphate method, a ribosome method or a DEAE dextran method can be used.

After the expression of the TAIP protein in prokaryotic cells or eukaryotic cells, isolation and purification of the desired protein from the culture can be conducted by a combination of known separation procedures. Examples thereof include treatment with a denaturant such as urea or a surfactant, ultrasonication, enzymatic digestion, salting, solvent precipitation, dialysis, centrifugal separation, ultrafiltration, gel filtration, SDS-PAGE, isoelectric focusing, ion exchange chromatography, hydrophobic chromatography, affinity chromatography and reverse phase chromatography.

Incidentally, the recombinant TAIP protein obtained by the foregoing method also includes fusion proteins with any other proteins. Examples thereof can include fusion proteins with glutathine-S-transferase (GST) and green fluorescent protein (GFP). Further, the proteins of the invention sometimes undergo various modifications in cells after translation. Accordingly, the modified proteins are also included in the range of the proteins of the invention. Examples of the modifications after translation can include elimination of N-terminal methionine, N-terminal acetylation, sugar chain addition, limited degradation with an intracellular protease, myristoylation, isoprenylation and phosphorylation.

The peptide of the invention is peptide fragment comprising a part of TAIP protein. This peptide can be prepared by cleaving the TAIP protein with any restriction enzyme. Further, it can also be formed by a known peptide synthesis method based on the amino acid sequences of SEQ ID No. 2, 4 or 6. Such peptide can be used as, for example, antigen for producing the antibody of the invention.

Figure 3:
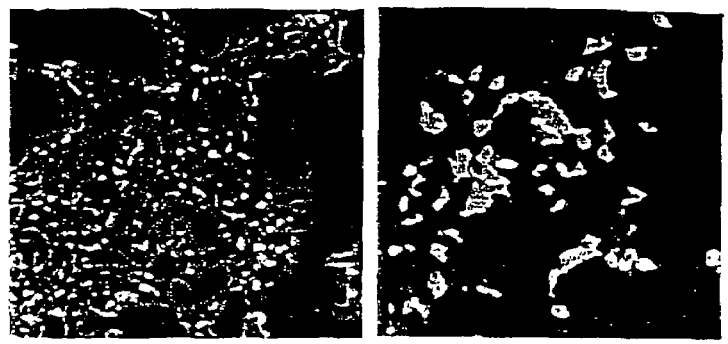
FIG. 3, the upper panels are phase-contrast and fluorescent micrograph of HEK293 cells, which were transfected with a plasmid encoding green fluorescent protein (GFP). The lower panels are light and fluorescent micrograph of HEK293 cells, which was transfected with plasmids encoding GFP fusion proteins with a full-length (Full), a N-terminal half (N-hall), and a C-terminal half (C-half) of SEQ ID No. 4 amino acid sequences. The left panels are the phase-contrast and the right panels are fluorescent micrographs.
Figure 3:
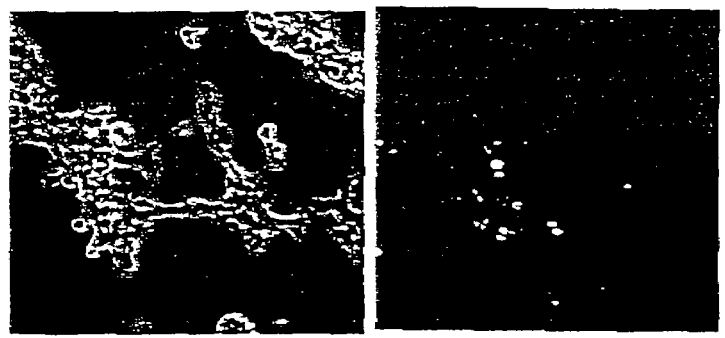
Figure 3:
Figure 3:
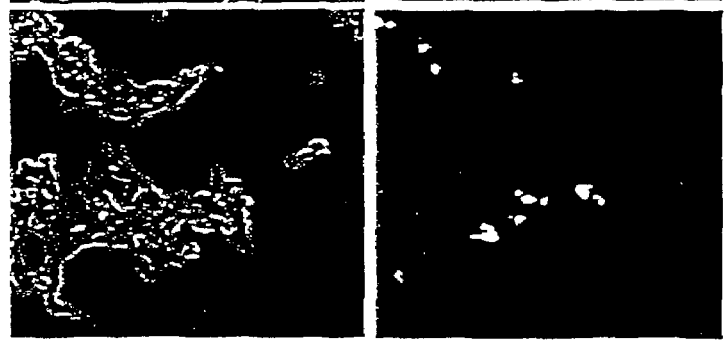
Figure 4:
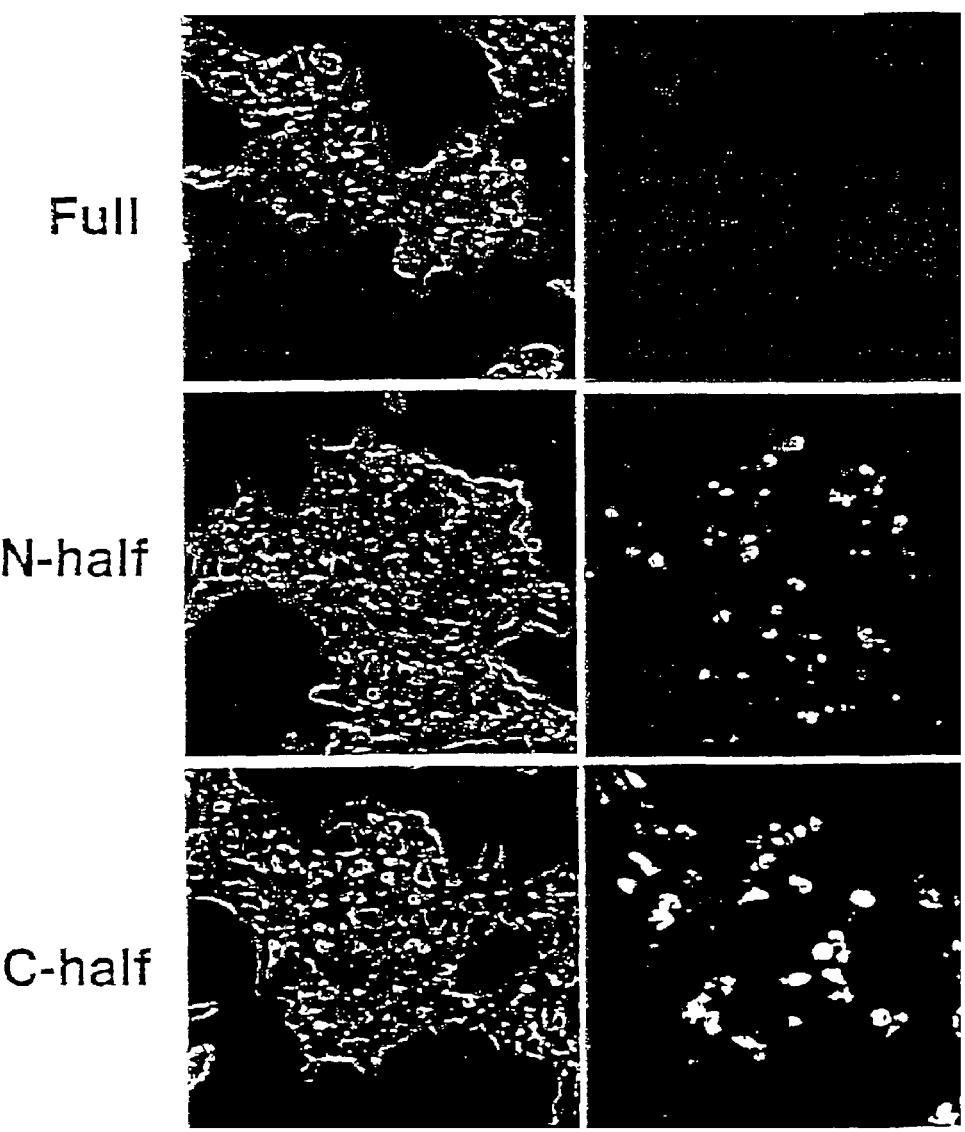
FIG. 4 is phase-contrast and fluorescent micrographs of HEK293, which were transfected with plasmids encoding GFP fusion proteins with a full-length (Full), a N-terminal half (N-half), and a C-terminal half (C-half) of SEQ ID No. 2 amino acid sequences. The left panels are the phase-contrast and the right panels are fluorescent micrographs.
Figure 5:
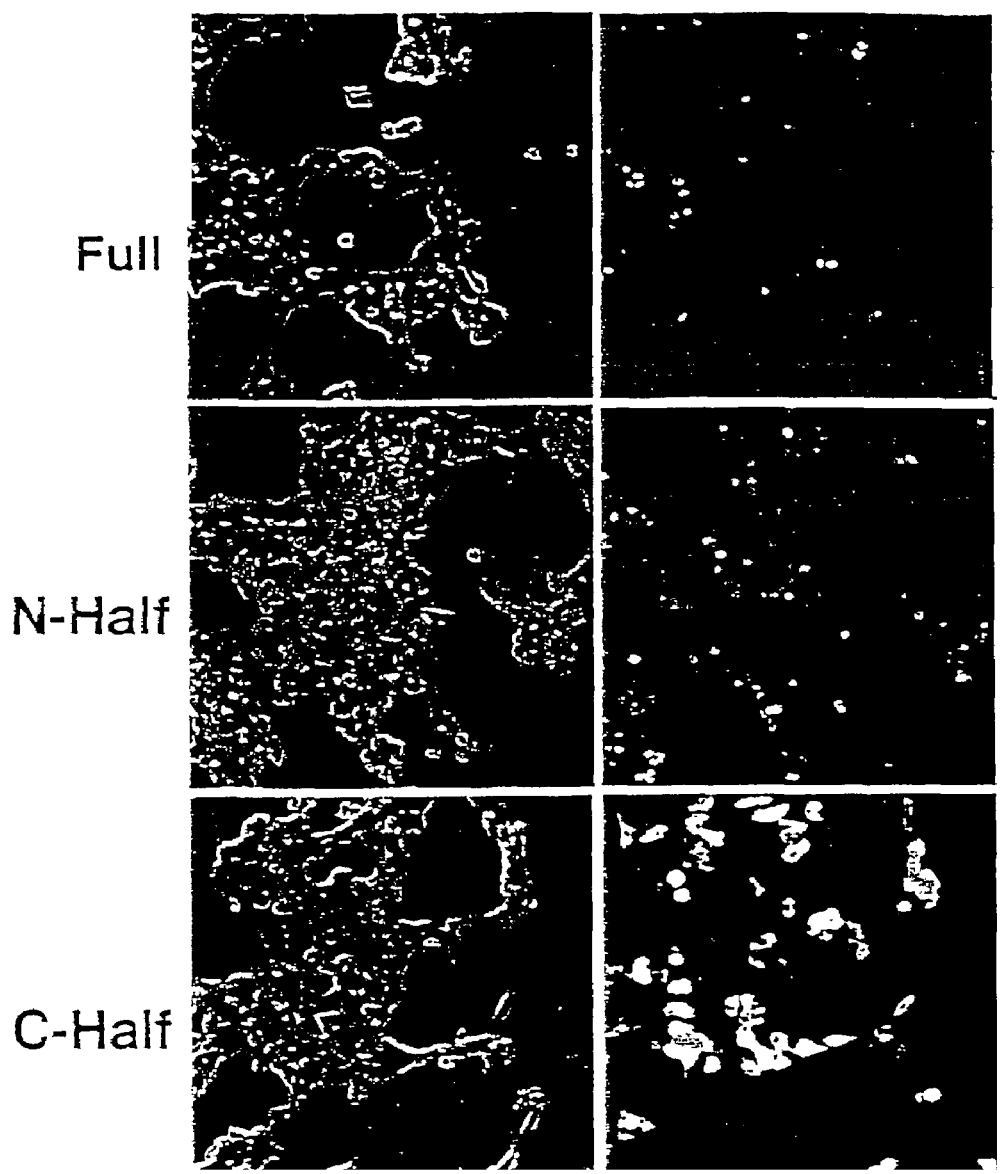
FIG. 5 is phase-contrast and fluorescent micrographs of HEK293, which were transfected with plasmids encoding GFP fusion proteins with a full-length (Full), a N-terminal half (N-half), and a C-terminal half (C-half) of SEQ ID No. 6 amino acid sequences. The left panels are the phase-contrast and the right panels are fluorescent micrographs.

Further, as preferable embodiments, the peptide of the invention include is a peptide consisting of at least five continuous amino acid residues of the 1st-328th amino acid sequence in SEQ ID No. 2, a peptide consisting of at least five continuous amino acid residues of the 1st-326th amino acid sequence in SEQ ID No. 4, and a peptide consisting of at least five continuous amino acid residues of the 1st-301st amino acid sequence in SEQ ID No. 6. That is, as shown in Example 6 to be described later, each of the TAIP proteins has an apoptosis induction activity on the N-terminal. Specifically, TAIP-3 has an apoptosis activity in a peptide of 1st-328th amino acid residues in SEQ ID No. 2, TAIP-2 in 1st-326th amino acid residues in SEQ ID No. 4 and TAIP-12 in a peptide of 1st-301st amino acid residues in SEQ ID No. 6 (FIGS. 3, 4 and 5). Accordingly, the peptide of at least five continuous amino acid residues in these regions can be used as a drug component of an apoptosis inducing agent or the like by combination with cell membrane penetration peptides such as HIV-TAT.

The other embodiment of the peptides of the invention is a peptide comprising at least 385th-389th amino acid sequence in SEQ ID No. 4. That is, the amino acid sequence (Asp-Asp-Asp-Asp-Lys) is known to be a recognition sequence of a bovine enterokinase (Biochemistry 16(15): 3354-3360, 1977). A molecule controlling an activity of the human apoptosis-related protein TAIP can be specified by screening a human enterokinase family with the peptide containing this sequence as a reporter.

The antibody of the invention is polyclonal antibody or monoclonal antibody which recognizes the purified human TAIP protein. Specifically, it is the antibody prepared using the purified TAIP protein or partial peptide thereof as antigen. The antibody of the invention includes the whole molecules Fab, F(ab')$_2$ and Fv fragments and the like that all can bind to epitopes of the TAIP protein. Such antibody can be obtained from a serum after animal immunized with the TAIP protein or the peptide as antigens. Alternatively, introducing the expression vector for eukaryotic cells into the muscle or the skin of animal through injection or a gene gun and then collecting the serum can produce the antibody. As animals, mice, rats, rabbits, goats, chickens and the like can be used. When B cells collected from the spleen of immunized animal are fused with myelomas to form hybridomas, monoclonal antibody can be produced. This antibody can be used, for example, to detect the expression of the TAIP gene.

EXAMPLES

The present inventions are described in more detail and more specifically with reference to Examples below, but are not to be constructed to be limited thereto. Basic manipulations and enzymatic reactions for DNA recombination are performed according to the reference ["Molecular Cloning, Laboratory Manual" Cold Spring Harbor Laboratory, 1989]. Restriction enzymes and various modification enzymes produced by Lifetech Oriental Inc. were used unless otherwise specified. Composition of buffer and conditions employed in each enzymatic reaction followed the attached instructions.

Example 1

Cloning of TAIP-3

According to the method described in the reference [Aidyama N. et al. Mol. Cell. Biology p.3266-3273, (2000)], human lung adenocarcinoma cell line (A549) were subjected to the gene trap method to allow to select cell clones in which expression is enhanced by TGF-β. From one of these cell clones, the gene sequences of 5'-untranslated region and 3'-untranslated region of cDNA clone (TAIP-3) were obtained as a trapped gene.

On the basis of the information, using 27mer sense primer (oligonucleotide of SEQ ID NO 7) and 30mer antisense primer (oligonucleotide of SEQ ID NO 8), the regions were amplified by PCR using cDNAs prepared from mRNAs extracted from human fibroblast MRC-5 cells as templates. After blunting the PCR product with T4 polymerase, the resultant was subject to 5'phosphorylation by T4 polynucleotide kinase and then inserted into pBluescriptII SK- EcoRV site to make transformation to host *Escherichia coli* DH-5 α FT (Gibco BRL). The nucleotide sequence of the obtained clone was determined and the clone caused no amplification error during the reverse transcription reaction and PCR reaction was selected. The obtained clone TAIP-3 consisted of a total length of 2593 bp having a structure comprising 106 bp of 5'-untranslated region, 1767 bp of open reading frame (ORF) and 720 bp of 3'-untranslated region (SEQ ID NO. 1). The ORF encoded a protein comprising 589 amino acid residues (SEQ ID NO. 2).

Example 2

Cloning of TAIP-2

In the case of making a search of human genomic database using cDNA of TAIP-3 determined in Example 1 (SEQ ID NO. 1), genomic DNA clone of Chromosome 2 (GenBank: AC023867) showed homology. Using 28mer sense primer (oligonucleotide of SEQ ID NO. 9) and 30mer antisense primer (oligonucleotide of SEQ ID NO. 10), the homologous cDNA fragment was amplified by PCR using plasmid DNA extracted from commercial library prepared from human fetal brain (ProQuest Two-Hybrid Human Fetal Brain cDNA Library: Life Technologies Inc., catalogue number: 11386-018) as a template. After blunting the PCR product with T4 polymerase, the resultant was subject to 5'phosphorylation by T4 polynucleotide kinase and then inserted into pBluescriptII SK-EcoRV site to make transformation to host *Escherichia coli* DH-5 α FT (Gibco BRL). The nucleotide sequence of the obtained clone was determined and the clone caused no amplification error during the reverse transcription reaction and PCR reaction was selected. The obtained clone TAIP-2-part consisted of a total length of 301 bp and corresponded with the partial sequence of the database clone (GenBank: AC023867). The obtained insert was used as a probe, commercial library prepared from human fetal brain (ProQuest Two-Hybrid Human Fetal Brain cDNA Library: Life Technologies Inc., catalogue number: 11386-018) was subject to screening by hybridization using a radioisotope to obtain a clone (TAIP-2). The obtained clone consisted of a total length of 2975 bp having a structure comprising 263 bp of 5'-untranslated region, 1755 bp of ORF, and 957 bp of 3'-untranslated region (SEQ ID NO .3). The ORF encoded a protein comprising 585 amino acid residues (SEQ ID NO. 4).

Example 3

Cloning of TAIP-12

In the case of making a search of human genomic database using cDNA of TAIP-3 determined in Example 1 (SEQ ID NO. 1), genomic DNA clone of Chromosome 12 (GenBank: AC023648) showed homology. In the case of making a search again of human EST database using information from 5'-end sequence of the genomic clone, the clone (AA305194) was thought to include 5'-untranslated region of a cDNA homologous to TAIP-3.

In addition, two gene-specific 30mer oligonucleotide (SEQ ID NO. 11 and 12) were prepared for sense primer toward downstream of ORF from the sequences in the region of the genomic DNA clone of Chromosome 12 (GenBank AC023648) having homology with TAIP-3. Using these primers, 3'-RACE was performed by the method described in the reference [Akiyama N., et al Mol. Cell. Biology p.3266-3273, (2000)] using cDNA prepared from mRNA extracted from human lung adenocarcinoma cell line A549 as templates. To amplify all regions including ORF from these obtained sequences, using 30mer sense primer (oligonucleotide of SEQ ID NO. 13) and 29mer antisense primer (oligonucleotide of SEQ ID NO. 14) synthesized the regions were amplified by PCR using cDNA prepared from mRNA extracted from human fibroblast MRC-5 cells as a template. After blunting the PCR product with T4 polymerase, the resultant was subject to 5'phosphorylation by T4 polynucleotide kinase and then inserted into pBluescriptII SK-EcoRV site to make transformation to host *Escherichia coli* DH-5 α FT (Gibco BRL). The nucleotide sequence of the obtained clone was determined and the clone caused no amplification error during the reverse transcription reaction and PCR reaction was selected. The obtained clone TAIP-12 consisted of a total length of 1682 bp having a structure comprising 27 bp of 5'-untranslated region, 1629 bp of ORF and 26 bp of 3'-untranslated region (SEQ ID NO. 5). The ORF encoded a protein comprising 543 amino acid residues (SEQ ID NO. 6).

Example 4

Confirmation of Apoptosis by Expression of Tag Fusion Proteins on Human Cells

Using cDNAs of TAIP-3, TAIP-2, and TAIP-12 specified in Example 1, Example 2, and Example 3 respectively as templates, the translational region was amplified by the PCR method. The PCR primers used were as follows: a 36mer sense primer (oligonucleotide of SEQ ID NO. 15) and a 33mer antisense primer which was added XhoI site to immediately after the termination codon (oligonucleotide of SEQ ID NO. 16) in the case of TAIP-3, a 36mer sense primer to which added BamHI site (oligonucleotide of SEQ ID NO. 17) and a 33mer antisense primer, which was added XhoI site to immediately after the termination codon (oligonucleotide of SEQ ID NO. 18) in the case of TAIP-2, and a 36mer sense primer to which is added BamHI site (oligonucleotide of SEQ ID NO. 19) and a 33mer antisense primer added SalI site immediately after the termination codon (oligonucleotide of SEQ ID NO. 20) in the case of TAIP-12.

The PCR product was purified and cleaved with a restriction enzyme in which a recognition site is added to each primer. After the obtained insert was inserted into an unique site from BamHI site to XhoI site of a modified vector (pFMH-3.1), in which tags and multicloning sites from NheI site to AflII site of a Tag fusion protein expression vector (pcDNA3.1/myc-His(-)B: Invitrogen) are substituted for cDNA of SEQ ID NO. 21, the resultant plasmid was transformed to host *Escherichia coli* DH-5αFT (GibcoBRL). The nucleotide sequence was confirmed and a clone expressing Myc tag and His tag as a fusion protein on the C-terminal of ORF in each cDNA was selected. The clone was cultured in LB culture medium at 37° C. for 16 hours to purify an expression plasmid DNA.

Figure 2:
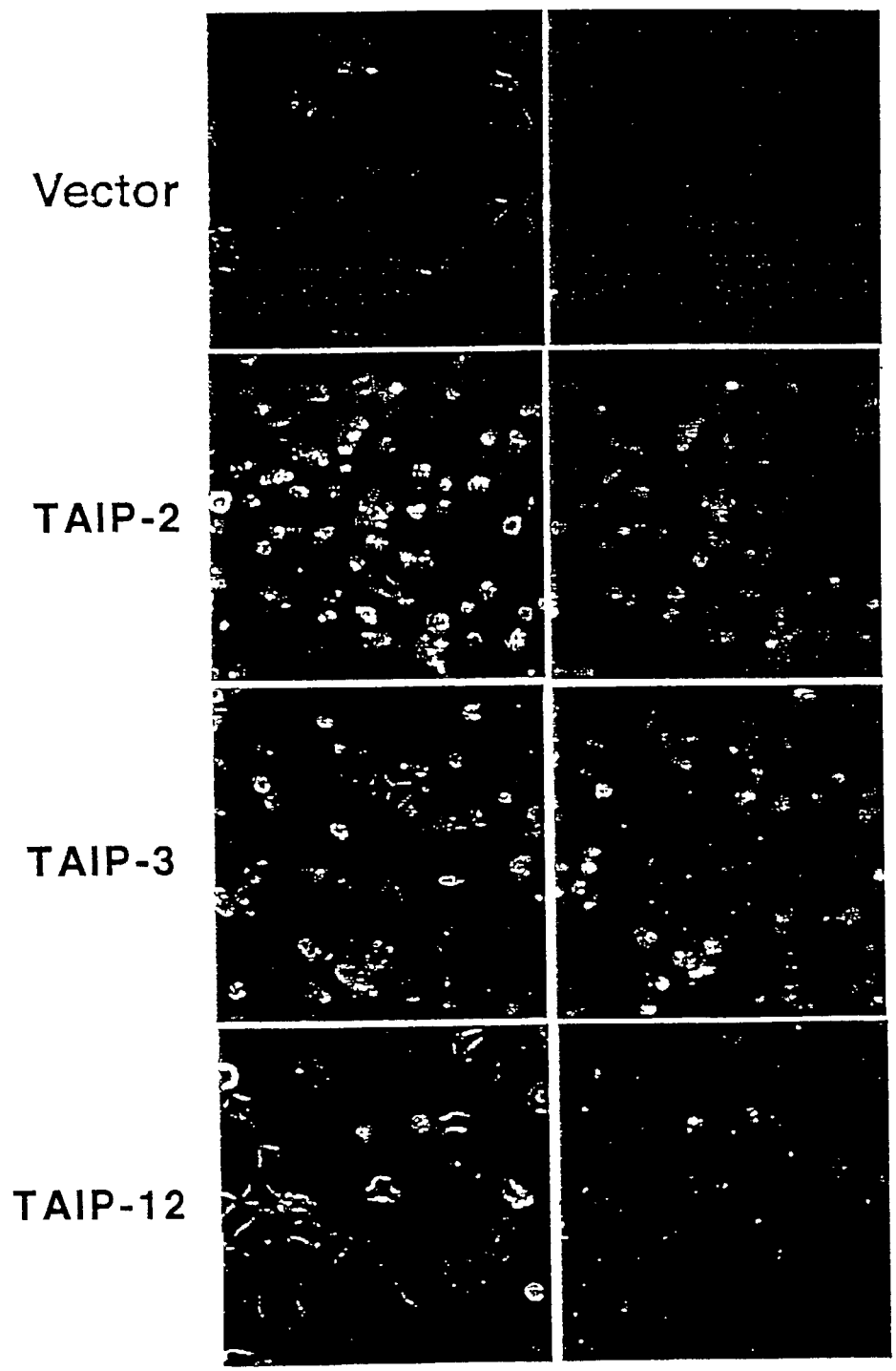
FIG. 2 is phase-contrast and fluorescent micrographs as same as FIG. 1 except that NTERA-2, a human pluripotent embryonal carcinoma cell line was used.

The plasmids were introduced into human lung adenocarcinoma cell line A549 cells, human embryo kidney cell line HEK293, and human teratocarcinoma cell line NTERA-2 according to attached instructions of lipofectamin2000 (GibcoBRL), 24 hours thereafter the cells were treated with an reagent detecting apoptotic cells, fluorescent-labeled Annexin V (Medical and Biological Laboratory) and a marker pigment for dead cells, PI (propidium iodide), and 15 minutes thereafter observations under a fluorescence microscope revealed the cells cause apoptosis (FIGS. 1 and 2).

Example 5

Confirmation of Apoptosis by Expression of Fusion Protein Comprising Green Fluorescent Protein (GFP) and Full Length Protein Using cDNAs of TAIP-3, TAIP-2, and TAIP-12 specified in Example 1, Example 2, and Example 3 respectively as templates, the tanslational region was amplified by the PCR method. The PCR primers used were as follows: a 46mer sense primer to which added Kozak initiation sequence and BamHI site (oligonucleotide of SEQ ID NO. 22) and a 33mer antisense primer which was added XhoI site to immediately after the termination codon (oligonucleotide of SEQ ID NO. 23) in the case of TAIP-3, a 43mer sense primer to which added Kozak initiation sequence and BamHI site (oligonucleotide of SEQ ID NO. 24) and a 33mer antisense primer which was added XhoI site to immediately after the termination codon (oligonucleotide of SEQ ID NO.25) in the case of TAIP-2, and a 43mer sense primer to which is added Kozak initiation sequence and BamHI site (oligonucleotide of SEQ ID NO. 26) and a 34mer antisense primer added SalI site immediately after the termination codon (oligonucleotide of SEQ ID NO. 27) in the case of TAIP-12. The obtained PCR product was purified and cleaved with a restriction enzyme in which a recognition site was added to each primer. After the obtained insert was inserted into from BamHI site to XhoI site of a GFP expression vector (pEGFP-N3: Clontech), the resultant plasmid was transformed to host *Escherichia coli* DH-5αFT (GibcoBRL). The nucleotide sequence was confirmed and a clone expressing a protein allowing GFP to fuse to the C-terminal of ORF in each cDNA was selected. The clone was cultured in LB culture medium at 37° C. for 16 hours to purify an expression plasmid DNA.

The plasmids were introduced into human fetal hepatocyte line HEK293 and human teratocarcinoma cell line NTERA-2 according to attached instructions of lipofectamin2000 (GibcoBRL) and then 24 hours thereafter observations under a fluorescence microscope revealed the cells in which the fusion protein expressed showed typical image for apoptosis (FIGS. 3, 4, and 5).

Example 6

Confirmation of Apoptosis by Expression of Fusion Protein Comprising Green Fluorescent Protein (GFP) and N-Terminal or C-Terminal Region of Each Protein Using cDNAs of TAIP-3, TAIP-2, and TAIP-12 specified in Example 1, Example 2, and Example 3, respectively, as templates, the N-terminal and C-terminal regions, respectively, were amplified by PCR method. In the case of N-terminal region of TAIP-3 (amino acid position 1-328 of SEQ ID NO. 2), a 46mer sense primer to which added Kozak initiation sequence and BamHI site (oligonucleotide of SEQ ID NO. 22) and a 34mer antisense primer which was added XhoI site (oligonucleotide of SEQ ID NO. 28) were used and in the case of C-terminal region of TAIP-3 (position 328-589 of SEQ ID NO. 2) a 46mer sense primer to which added Kozak initiation sequence and BamHI site (oligonucleotide of SEQ ID NO. 29) and a 33mer primer which was added XhoI site to immediately after the terminatin codon (oligonucleotide of SEQ ID NO. 23) were used. In the case of N-terminal region of TAIP-2 (amino acid position 1-326 of SEQ ID NO. 4) a 43mer sense primer to which is added Kozak initiation sequence and BamHI site (oligonucleotide of SEQ ID NO. 24) and a 34mer antisense primer added XhoI site (oligonucleotide of SEQ ID NO. 30) were used and in the case of C-terminal region of TAIP-2 (position 327-585 of SEQ ID NO. 4) a 46mer sense primer to which added Kozak initiation sequence and BamHI site (oligonucleotide of SEQ ID NO. 31) and a 34mer antisense primer which was added XhoI site to immediately after the termination codon (SEQ ID NO. 25) were used. Further, in the case of N-terminal region of TAIP-12 (position 1-301 of SEQ ID NO. 6) a 43mer sense primer to which is added Kozak initiation sequence and BamHI site (oligonucleotide of SEQ ID NO. 26) and a 34mer antisense primer added SalI site (oligonucleotide of SEQ ID NO. 32) were used and in the case of C-terminal region (position 302-543 of SEQ ID NO. 6) a 46mer sense primer to which added Kozak initiation sequence and BamHI site (oligonucleotide of SEQ ID NO. 33) and a 34mer antisense primer which was added SalI site to immediately after the termination codon (oligonucleotide of SEQ ID NO. 27) were used. The obtained PCR product was purified and cleaved with a restriction enzyme in which a recognition site was added to each primer. After the obtained insert was inserted into from BglII site to SalI site of a GFP expression vector (pEGFP-N3: Clontech), the resultant plasmid was transformed to host *Escherichia coli* DH-5αFT (GibcoBRL). The nucleotide sequence was confirmed and a clone expressing a protein allowing GFP to fuse to the C-terminal region or C-terminus of N-terminal region of each protein was selected. The clone was cultured in LB culture medium at 37° C. for 16 hours to purify an expression plasmid DNA.

The each plasmid was transfected to human embryo kidney cells HEK293 and human teratocarcinoma cell line NTERA-2 according to attached instructions of lipofectamin2000 (GibcoBRL) and then 20 hours thereafter observations under a fluorescence microscope confirmed the cells in which the fusion protein of N-terminal region and GFP expressed showed typical image for apoptosis. Moreover, it was confirmed that no typical image for apoptosis was observed in the cells in which the fusion protein of C-terminal region and GFP were expressed. Therefore, it was turned out that even partial polypeptide of N-terminal region in each protein had a function inducing apoptosis. (FIGS. 3, 4, and 5)

Example 7

Induction of Expression by TGF-β

RNA was extracted from A549 cells (1×10⁸ cells), which were untreated or treated with TGF-β for 48 hours and analyzed by the Northern blot analysis. Using a 30mer sense primer initiating from the initiation codon (oligonucleotide of SEQ ID NO. 34) and a 30mer antisense primer up to immediately before the termination codon (oligonucleotide of SEQ ID NO. 35) of TAIP-3 cDNA (SEQ ID NO. 1), the translational region was amplified by PCR, the obtained product was used as a probe to allow hybridization, and it was confirmed that approximately 3 kb of mRNA was expressed in A549 cells and that expression of TAIP-3 was enhanced by TGF-β treatment.

Example 8

Tissue Distribution of TAIP

Multiple Tissue Northern blots (Clontech), which are blots of mRNA extracted from human tissues and human cancer cell lines on nylon membranes was hybridized with [³²P]dCTP-labeled probe prepared with Taip-2, 3 and 12 polynucleotides encoding C-terminal region of their products.

Figure 6:
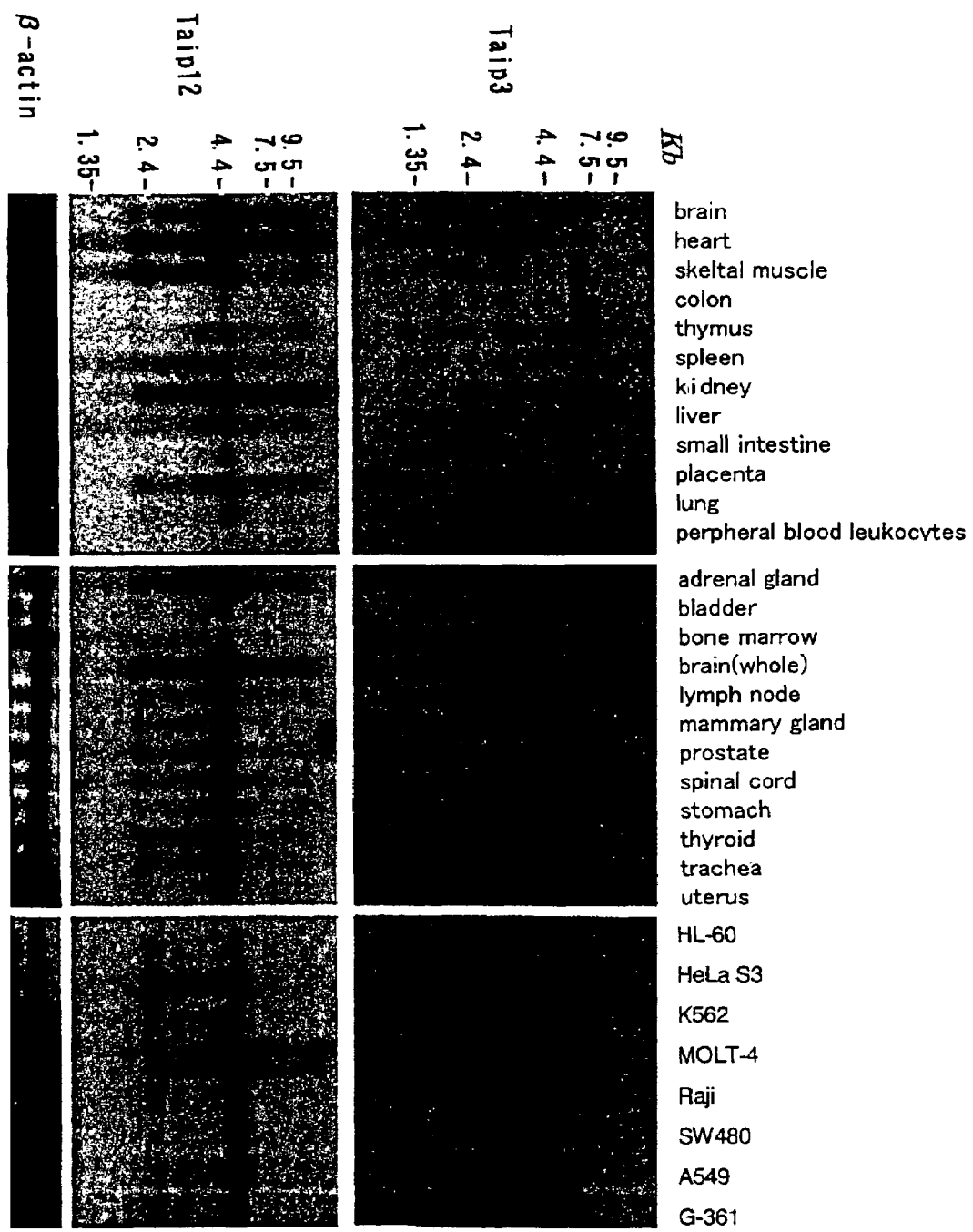
FIG. 6 is the results of northern blotting of poly (A)+RNA from Human tissues and human cancer cell lines, which were blotted on nylon membrane (Clontech) and hybridized with radiolabeled polynucleotide encoding C-terminus of TAIP-3 or -12 as probe. The transcripts of TAIP-3 and -12 (about 3.3 kb and 4.3 kb, respectively) were shown.

According to the results, Taip-3 is expressed high in lung, peripheral blood leukocytes, adrenal gland, mammary gland, and Taip-12 is expressed all the tissues examined and relatively high expression was observed in brain, heart, skeletal muscle, kidney, placenta and adrenal gland. Expression of Taip-2 was not detected in any tissue examined (FIG. 6 and data not shown).

Example 9

DNA Degradation Induced by TAIP

The plasmids encoding GFP fusion protein with full-length, N- or C-halves of Taip genes products or GFP only (control) were transfected to human embryo kidney cell line HEK293 with lipofectamin2000 (Gibco BRL) according to attached instructions. Twenty-four hours later, DNA contents of GFP expressing cells were analyzed with FACS-Calibur (BD Bioscience).

Figure 7:
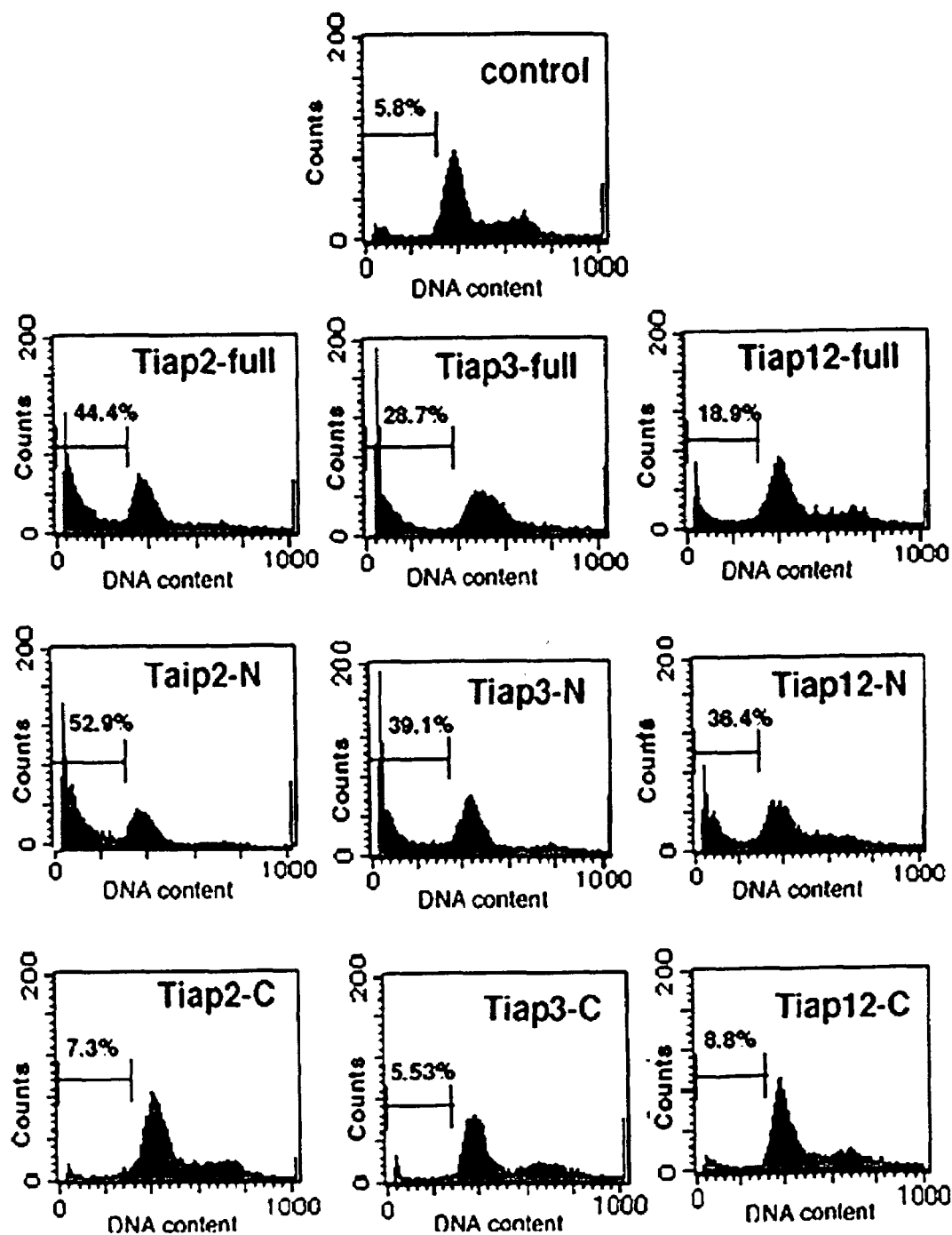
FIG. 7 is the result of FACS analysis for DNA contents of GFP expressing HEK239 cells, to which the plasmids encoding GFP fusion protein with various length of TAIP protein were transfected before 24 hours of the analysis.

According to the results, in the cells expressing fill-length or N-terminal region of TAIP proteins, DNA degradation were confirmed (FIG. 7).

Example 10

Caspase-3 Activation in TAIP Expressing Cells

Figure 8:
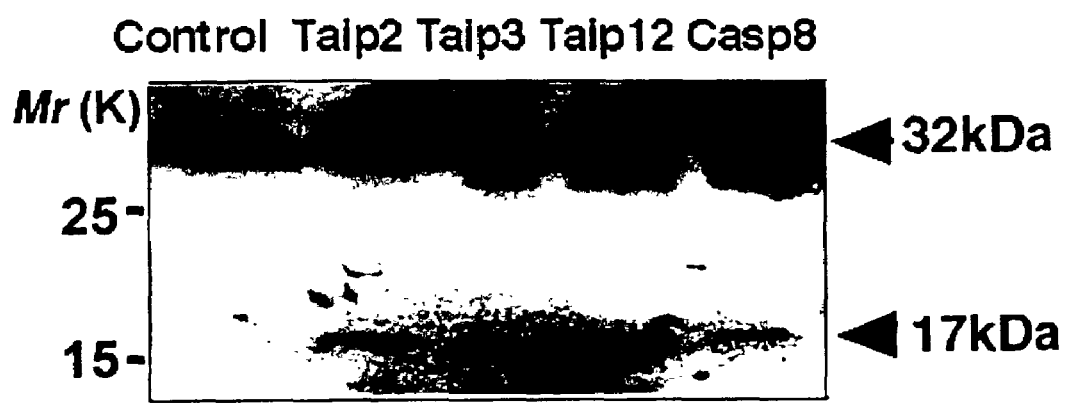
FIG. 8 is the result of western blotting for detecting active form of caspase-3, in which the plasmids encoding GFP fusion protein with TAIPs were transfected into HEK293 cells and cell lysates were prepared 24 h later. Each sample was electrophoresed on a 20% polyacrylamide gel, blotted onto a nitrocellulose filter and detected with an anti-caspase-3 polyclonal antibody.

The plasmids encoding GFP fusion protein with N-halves of Taip-2, 3, 12 gene products or GFP only (control) were transfected into human embryo kidney cell line HEK293 with lipofectamin2000 (Gibco BRL) according to attached instructions and cell lysates were prepared 24 h later. Each sample (30 µg) was electrophoresed on a 20% polyacrylamide gel, blotted onto a nitrocellulose filter and detected with an anti-caspase-3 polyclonal antibody (BD Bioscience). Active form of caspase-3 was detected as bands near 17 kDa in Taip gene transfectants. The results indicated that caspase-3 was activated in the transfectants of these plasmids (FIG. 8).

Example 11

Preparation of Anti-TAIP-3 Antibody and Endogenous TAIP-3 Protein Induction by TGF-β

Rabbit polyclonal antibody against TAIP-3 was prepared by using SEQ ID No. 36 as antigen according to a standard protocol. A549, a human lung adenocarcinoma cell line were treated with TGF-β for 0, 3, 6, 12 or 24 hrs and normal human hepatocytes were treated with TGF-β for 0, 3, 6, 12, 36 or 60 hrs. The cells treated with TGF-□ for indicated time were lysed and analyzed with western blotting with anti-TAIP3 antibody.

Figure 9:
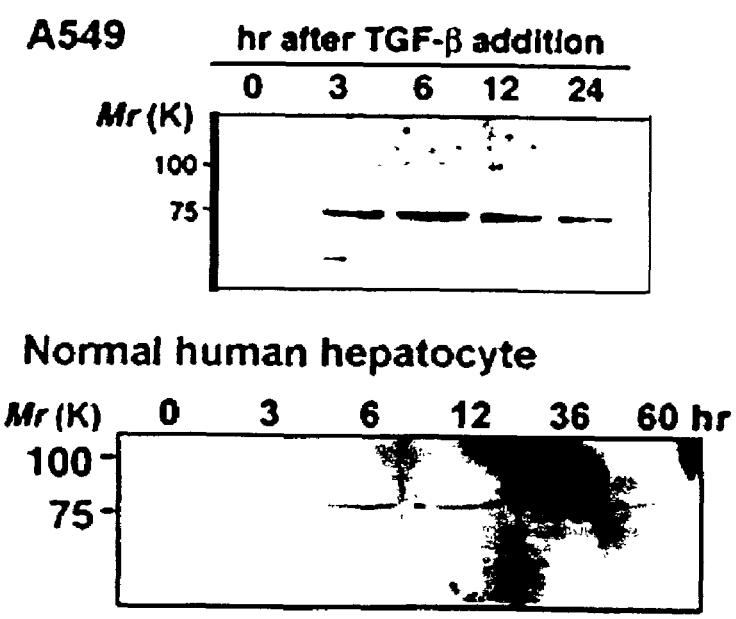
FIG. 9, the upper panel shows TAIP3 protein expression in A549, a human lung adenocarcinoma cell line, which were treated with TGF-β for 0, 3, 6, 12 or 24 hrs, lysed and analyzed with western blotting with anti-TAIP3 antibody. The lower panel showed TAIP3 protein expression in normal human hepatocytes, which were treated with TGF-β for 0, 3, 6, 12, 36 or 60 hrs, lysed and analyzed with western blotting with anti-TAIP3 antibody.

The results indicated that TAIP-3 was not detected in human lung adenocarcinoma cell line A549 before TGF-β treatment, and detected 3 to 5 hrs after TGF-β treatment (FIG. 9). In A549 cells, which do not undergo apoptosis by TGF-β, TAIP-3 expression decreased at 24 hr after TGF-β addition (FIG. 9, Upper panel) while in normal human hepatocytes, which undergo apoptosis by TGF-β, TAIP3 expression can be detected even 60 hrs after TGF-β addition (FIG. 9, Lower panel).

Example 12

Subcellular Localization of TAIP-3 in TGF-β Treated Cells

A549 cells, normal human hepatocytes and HLF a non-differentiated hepatoma cell line (obtained from Health Science Research Resources Bank) were treated with TGF-β, fixed and permealized with Triton-X100. The subcellular localization of TAIP-3 in these cells was observed by conforcal microscope after treatment with anti-TAIP3 and Cy3-conjugated secondary antibodies (Jackson ImmunoResearch).

Figure 10:
FIG. 10, the upper panel shows a confocal micrographs of A549 cells, which were cultured with TGF-β for 12 hr, fixed, permealized with Triton-X100 and treated with anti-TAIP3 antibody followed by Cy3-conjugated secondary antibody. The lower panel shows a confocal micrographs of a human hepatoma cell line, which was cultured with TGF-β for 48 or 60 hr, fixed, permealized with Triton-X100 and treated with anti-TAIP3 antibody followed by Cy3-conjugated secondary antibody.
Figure 10:
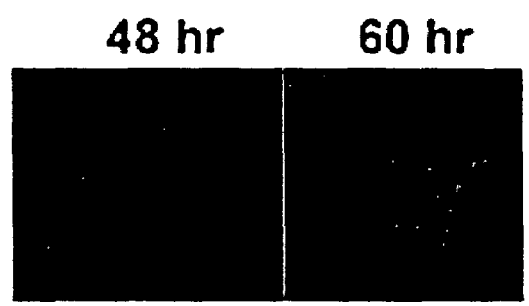

In A549 cells, TAIP3 was observed around the nucleus after 12 hr TGF-β treatment (FIG. 10, Upper panel) but gradually became undetectable thereafter. On the other hand, in normal human hepatocytes and HLF cells, TAIP3 was detected as small lumps around the nucleus and then the cells with crumpled nuclei were observed as small aggregates (FIG. 10, Lower panel), resulted in apoptosis.

Example 13

Caspase-3 Activation in TAIP-3 Expressing Cells

Figure 11:
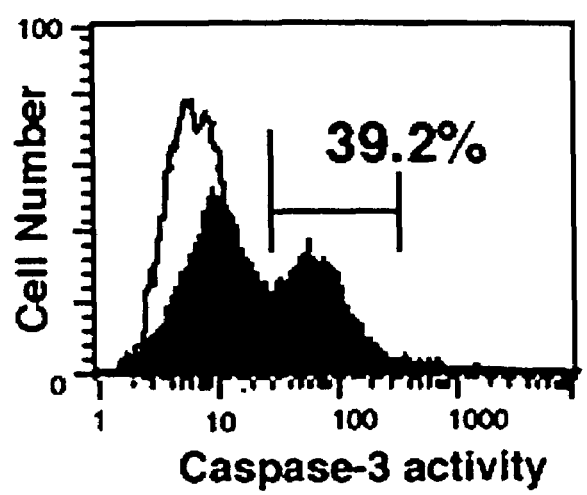
FIG. 11 is the result of FACS analysis for caspase-3 activity, in which normal human hepatocytes were treated with TGF-β for 24 h and were further treated with PhiPhiLux™G1D2kit. Blue line shows caspase-3 activity before treatment of TGF-β and red line shows that of after treatment of TGF-β.
Figure 12:
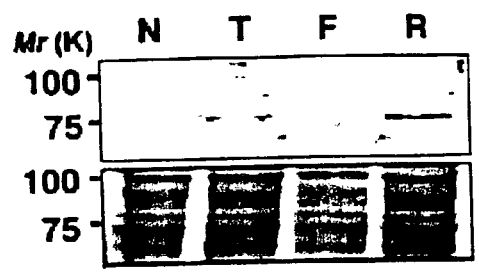
FIG. 12 shows TAIP-3 expression by western blotting. HLF cells were cultured with TGF-β for 24 h. Untreated cells (N) and TGF-β-treated total cell (T), flat cell (F) and round cell (R) populations were analyzed with anti-TAIP-3 antibody.

Normal human hepatocytes and HLF human hepatoma cell line were treated with PhiPhiLux™G1D2kit (OncoImmunin) after culturing in the presence or absence of TGF-β for 24 hr and caspase-3 activation in the cells treated with TGF-β were detected with flow cytometry (FIG. 11). In these cells with activated caspase-3, higher level of TAIP-3 expression was detected by western blot analysis with anti-TAIP-3 antibody (FIG. 12, Upper panel). The lower panel shows proteins on the immunoblot filter stained with amid black.

From the results shown in examples 11 to 13 revealed the strong correlation between TAIP-3 expression and TGF-β-induced apoptosis.

Example 14

Anti-TAIP Antibody and Detection of TAIP-2 in a Brain Disorder

Figure 13:
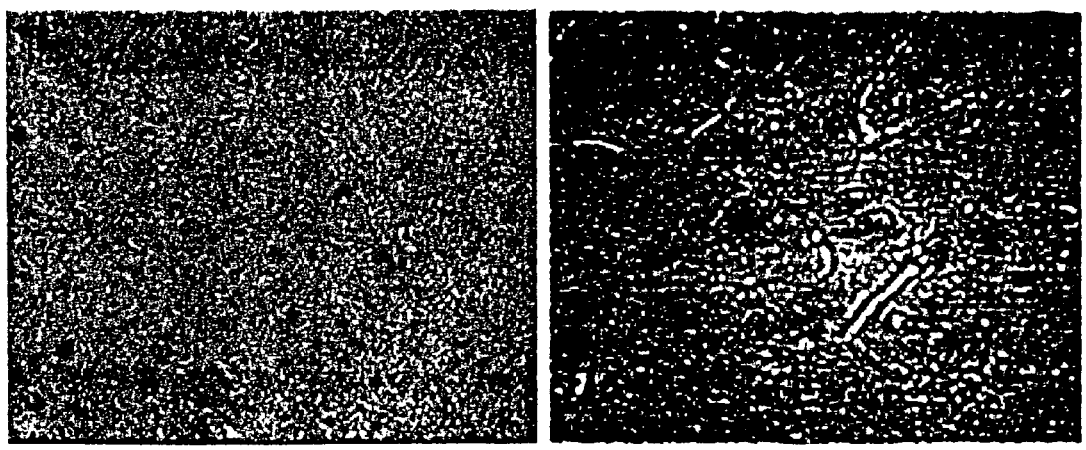
FIG. 13 is photographs of a brain section, which was prepared from the brain with focal ischemic damage, fixed onto a slideglass, treated with preimmuno serum (left) or anti-TAIP-2 polyclonal antibody (right) and then treated with LSAB kit (DAKO) for detecting the antibody. The portions recognized with the antibody were stained as reddish-brown.

Rabbit polyclonal antibody against TAIP-2 was prepared by using SEQ ID No. 37 according to a standard protocol. The section prepared from the brain with focal ischemic damage was Immunohistochemiclly analyzed with anti-TAIP2 antibody by using LSAB kit (DAKO). Although no significant staining was observed with preimmuno serum, significant spotted staining was observed with anti-TAIP-2 antibody (FIG. 13). These results indicate that TAIP2 can be expressed in the brain with focal ischemic damage and suggested that anti-TAIP-2 antibody may be useful for diagnosis of the brain disorders induced by apoptosis.

INDUSTIAL APPLICABILITY

As mentioned above in detail, the present invention provides novel human proteins relating to apoptosis and the antibodies useful for the diagnosis, therapy, and etc. of apoptosis-related diseases such as cancer and autoimmune disease. Also, the utilization of the cDNA of the invention enables the mass production of the above proteins. And a screening of low molecular compounds bound to the proteins enables the search for pharmaceuticals such as a new type of antitumor drug.

The invention claimed is:

1. A purified human apoptosis-related protein comprising the amino acid sequence of SEQ ID NO: 2.

2. The purified human apoptosis-related protein of claim 1, which is an expression product of a human apoptosis-related gene that encodes a human apoptosis-related protein, and said protein is produced by a transformant, which has been transformed with a recombinant vector comprising a polynucleotide encoding the human anoptosis-related protein having the amino acid sequence of SEQ ID NO: 2.

3. A purified or synthesized peptide, 1st328th amino acids of SEQ ID NO:2.

* * * * *